(12) United States Patent  (10) Patent No.: US 9,120,808 B2
Bulusu  (45) Date of Patent: Sep. 1, 2015

(54) SUBSTITUTED CLAVULANIC ACID

(75) Inventor: Atchyuta Rama Chandra Murty Bulusu, Perchtoldsdorf (AT)

(73) Assignee: NABRIVA THERAPEUTICS AG, Vienna (AT)

( * ) Notice: Subject to any disclaimer, the term of this patent is extended or adjusted under 35 U.S.C. 154(b) by 0 days.

(21) Appl. No.: 13/395,606

(22) PCT Filed: Aug. 12, 2010

(86) PCT No.: PCT/AT2010/000297
§ 371 (c)(1),
(2), (4) Date: May 25, 2012

(87) PCT Pub. No.: WO2011/032192
PCT Pub. Date: Mar. 24, 2011

(65) Prior Publication Data
US 2012/0232047 A1   Sep. 13, 2012

(30) Foreign Application Priority Data
Sep. 15, 2009 (AT) ................ A 1458/2009

(51) Int. Cl.
*C07D 498/04* (2006.01)

(52) U.S. Cl.
CPC ................... *C07D 498/04* (2013.01)

(58) Field of Classification Search
CPC ................................. C07D 498/04
USPC ....... 540/347, 348, 349; 514/210.06
See application file for complete search history.

(56) References Cited

U.S. PATENT DOCUMENTS

| | | | |
|---|---|---|---|
| 4,167,630 A | 9/1979 | Firestone | |
| 4,206,120 A | 6/1980 | Hunt | |
| 4,293,555 A | 10/1981 | Christensen et al. | |
| 4,742,052 A * | 5/1988 | Sunagawa et al. | 514/195 |

FOREIGN PATENT DOCUMENTS

| | | |
|---|---|---|
| EP | 0 018 305 A1 | 10/1980 |
| EP | 0 028 083 A1 | 5/1981 |
| EP | 0 050 932 A1 | 5/1982 |
| EP | 0 126 587 A1 | 11/1984 |
| EP | 0 162 193 A1 | 11/1985 |
| EP | 0 574 940 A1 | 12/1993 |
| FR | 2 340 321 A1 | 9/1977 |
| WO | 03/055856 A2 | 7/2003 |

OTHER PUBLICATIONS

Wiberg, Nils. Inorganic Chemistry. Academic Press: San Diego. 2001.*
Reading et al., "Structure-Activity Relationships Amongst Beta-Lactamase Inhibitors", Journal of Enzyme Inhibition, New York, vol. 1, No. 2, Jan. 1, 1986, pp. 83-104.

* cited by examiner

*Primary Examiner* — Golam M M Shameem
*Assistant Examiner* — Laura Daniel
(74) *Attorney, Agent, or Firm* — Maschoff Brennan

(57) ABSTRACT

The present invention relates to compounds of formula I

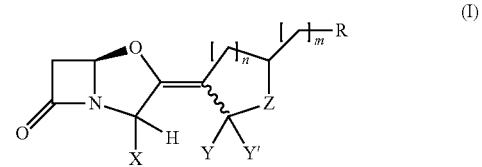

and to compounds of formula II

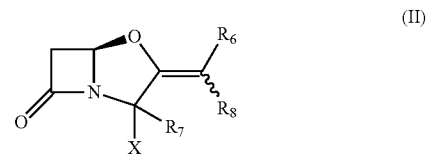

wherein the substituents have various meanings. These compounds are useful as beta lactamase inhibitors.

20 Claims, 1 Drawing Sheet

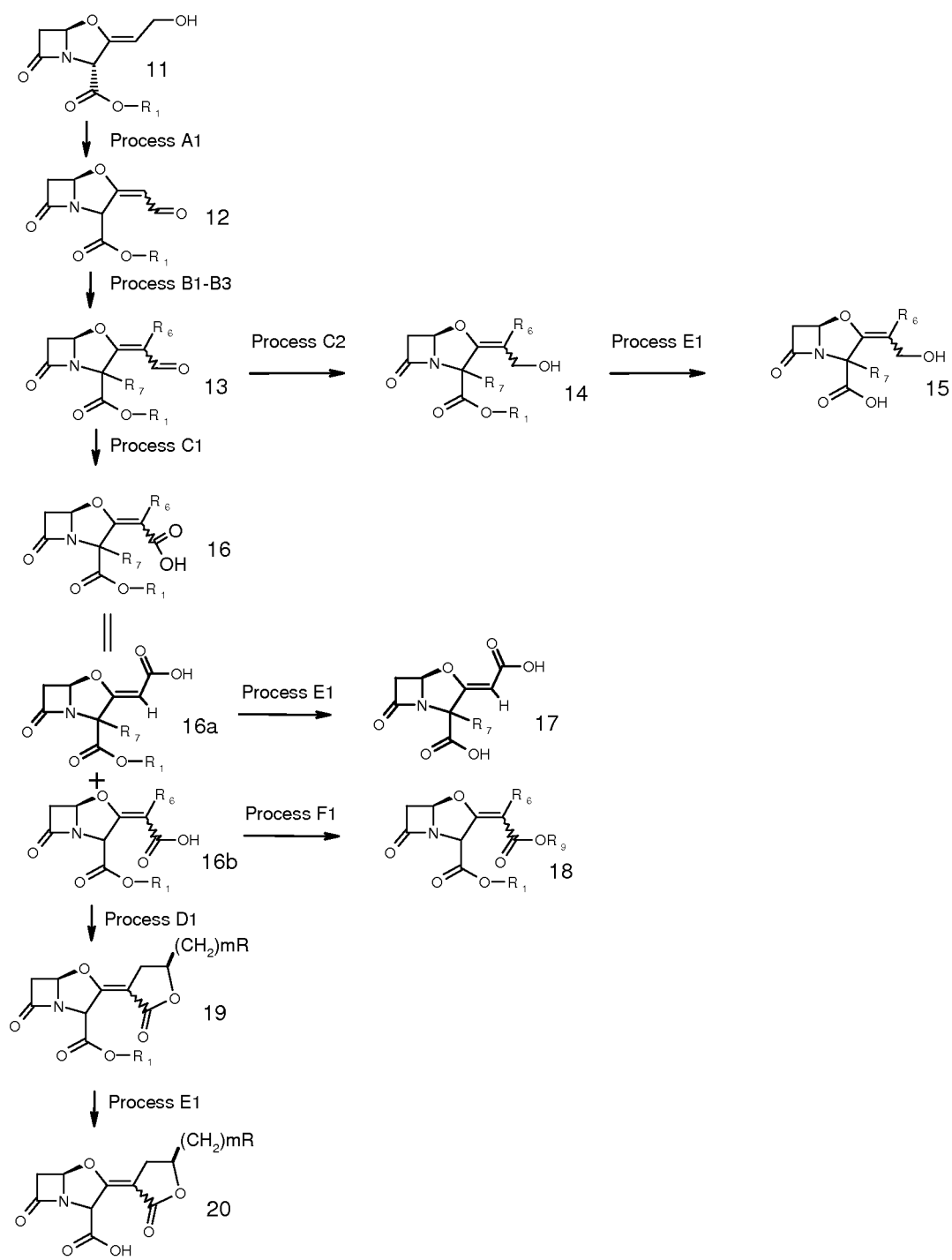

SUBSTITUTED CLAVULANIC ACID

The present invention relates to organic compounds and their intermediates, their uses as well as a pharmaceutical composition comprising such a compound or its intermediate.

Since bacteria become resistant to antibiotics there is an increasing demand in the art to develop more effective antibiotics. It has been found that clavulanic acid is a very potent β-lactamase inhibitor. Especially a combination of clavulanic acid with amoxicillin has been found to be very effective and is marketed as Augmentin.

The technical problem underlying the present invention is the provision of organic compounds, namely clavams, having an improved antibiotic activity alone or in combination with other antibiotics and which overcome drawbacks of the prior art.

This problem is solved by a compound of formula I

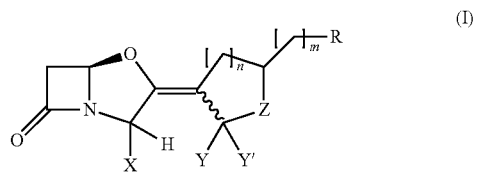

(I)

wherein
X is COOH or a salt thereof,
  $COOR_1$, wherein $R_1$ is $C_{1-4}$ alkyl which is optionally substituted,
  $CONR_2R_3$, wherein $R_2$ and $R_3$ independently represent H or $C_{1-5}$ alkyl which optionally contains one or more hetero atoms selected from O, S and N and/or is optionally substituted, or
  $CON(R_2)$—$CH(R_4)$—$R_5$, wherein
    $R_2$ is as defined above,
    $R_4$ is a group usually found in the α position of α-amino acids, and
    $R_5$ is COOH or salts thereof; $COOR_1$, wherein $R_1$ is as defined above; or
    $CONR_2R_3$, wherein $R_2$ and $R_3$ are as defined above,
Y and Y' are both H or together represent =O,
Z is O, $NR_2$ or N—$CH(R_4)$—$R_5$, wherein $R_2$, $R_4$ and $R_5$ are as defined above,
n is 1 or 2,
m is a number from 0 to 4,
R is H, or
  a saturated or unsaturated chain containing 1 to 8 carbon atoms, which is optionally substituted with a 5 or 6-membered nonaromatic ring containing one or more hetero atoms selected from O, S and N, or is substituted by aryl, alkyl or cycloalkyl, optionally contains one or more hetero atoms selected from O, S and N, halogen atoms selected from Cl, Br, I and F and/or azido $N_3$.

In formula I as well as in the formulas below, a jagged bond (∿∿∿ oder ∿∿∿-bond) attached to a double bond represents both E- and Z-isomer of the specific compound. Therefore, E- as well as Z-isomers are described by said formulas.

According to a preferred embodiment, the salt is a pharmaceutically acceptable salt, preferably a potassium salt.

According to another preferred embodiment, $R_1$ is methyl, preferably substituted by a pivaloyloxy group.

Preferably, $R_2$ and $R_3$ are independently substituted by $C_{1-4}$ alkyl or $C_{5-6}$ cycloalkyl.

A preferred embodiment is characterized in that $R_4$ is methyl or a benzyl group.

In a further preferred embodiment, R is a saturated or unsaturated chain containing 1 to 8 carbon atoms which is substituted by a 5 or 6-membered nonaromatic ring containing one or more hetero atoms selected from O, S and N, aryl, $C_{1-4}$ alkyl or $C_{5-6}$ cycloalkyl.

According to another preferred embodiment, R is a saturated or unsaturated chain containing 1 to 8 carbon atoms which is substituted by one or more hetero atoms selected from O, S, and N, wherein the O and S heteroatoms are protected as esters, carbonates or ethers, and the N heteroatoms are alkylated or protected as amides or carbamates.

A particularly preferred compound of formula I is defined by formula III.

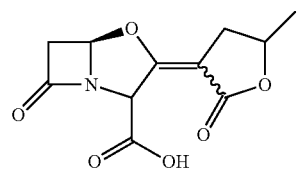

According to a further aspect, the present invention provides intermediates of formula II

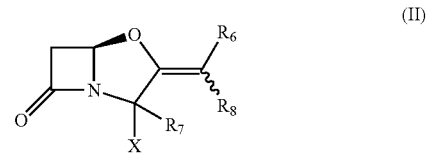

(II)

wherein
X is as defined in formula I,
either $R_6$ or $R_7$ is H, with the proviso that
  if $R_7$ is H, $R_6$ is a saturated or unsaturated chain containing 1 to 11 carbon atoms, which is optionally substituted by a 5 or 6-membered nonaromatic ring containing one or more hetero atoms selected from O, S and N, or with aryl, alkyl or cycloalkyl, optionally contains one or more hetero atoms of O, S and N, and/or is optionally substituted with one or more atoms selected from the hetero atoms of O, S and N, halogens of Cl, Br, I and F and/or azido $N_3$,
or vice versa; and
$R_8$ is COOH, $CH_2OH$ or CHO.

Intermediates of formula II are useful as starting materials for the production of compounds of formula I. However, they also exhibit antmicrobial activity and can be used as antibiotics, alone or in combination with other antibiotics.

According to a preferred embodiment, $R_6$ or $R_7$, respectively, is a saturated or unsaturated chain containing 1 to 11 carbon atoms which is substituted by a 5 or 6-membered nonaromatic ring containing one or more hetero atoms of O, S and N, or with aryl, $C_{1-4}$ alkyl or $C_{5-6}$ cycloalkyl.

According to another preferred embodiment, $R_6$ or $R_7$, respectively, is a saturated or unsaturated chain containing 1 to 11 carbon atoms which is substituted by one or more hetero atoms selected from O, S, and N, wherein the O and S heteroatoms are protected as esters, carbonates or ethers, and the N heteroatoms are alkylated or protected as amides or carbamates.

A particularly preferred compound of formula II is defined by formula IV.

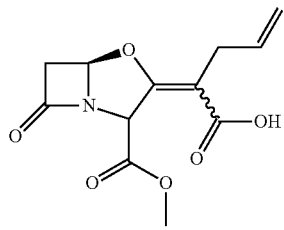

(IV)

Another preferred compound of formula II is defined by formula V.

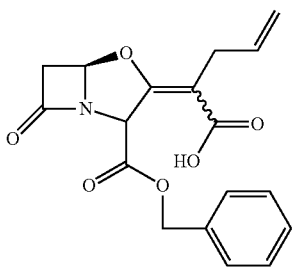

(V)

The compounds of the present invention may exist in the form of isomers and mixtures thereof, e.g. including diastereoisomers and mixtures thereof. Isomeric mixtures may be separated if necessary, e.g. according to a method as conventional, to obtain pure isomers.

The present invention includes a compound of the present invention in any isomeric form and in any isomeric mixture.

The compounds of the present invention may also exist in the form of solvates, for example, hydrates.

According to a further aspect, the invention provides the compounds of formula I and formula II, respectively, for use as a medicament.

The compounds of the present invention have been found to be useful as β-lactamase inhibitors, antimicrobial substances and antibiotics, alone or in combination with other antibiotics.

The compounds of the present invention are particularly useful in that, when administered to a mammal, the effectiveness of a co-administered β-lactam antibiotic against β-lactamase producing bacteria will be enhanced.

The compounds of the present invention may be used alone or in combination therapy with β-lactam antibiotics, to treat infections of, inter alia, the respiratory tract, the urinary tract and soft tissues in humans.

According to another aspect, the invention provides a pharmaceutical composition comprising a compound of formula I and/or formula II, which optionally further comprises a β-lactam antibiotic belonging to the class of penicillins or cephalosporins. Typically, when combined together in a pharmaceutical composition, the weight ratio of β-lactam antibiotic to the compound of the present invention is between about 15:1 and about 1:1.

Pharmaceutical compositions of the present invention may be used to treat infections in mammals. Bacterial infections amenable to treatment by the compounds and the compositions of the present invention include, but are not limited to, respiratory diseases including community acquired *pneumoniae*, acute exacerbations of chronic bronchitis and acute bacterial sinusitis, caused by respiratory pathogens, such as *Haemophilus influenzae* and *Moraxella catarrhalis* including antibiotic resistant isolates.

Further, bacterial infections amenable to treatment by pharmaceutical compositions of the present invention which contain an antibiotic include, but are not limited to, pediatric otitis media, sinusitis, pneumonia, acute exacerbations of bronchitis in adults caused by *H. influenzae* or *Streptococcus pneumoniae*, including drug resistant *S. pneumoniae* such as penicillin resistant *S. pneumoniae*, soft tissue infections caused by *E. coli, Klebsiella pneumoniae, Enterobacter* spp. and all other members of the family Enterobacteriaceae, and infections caused by β-lactamase producing, methicillin susceptible staphylococci and β-lactamase producing anaerobes.

For treatment, the appropriate dosage will, of course, vary depending upon, for example, the chemical nature and the pharmakokinetic data of a compound of the present invention employed, and the individual host, the mode of administration and the nature and severity of the conditions being treated. However, in general, for satisfactory results in larger mammals, for example humans, an indicated daily dosage is in the range from about 0.01 g to about 2.0 g of a compound of the present invention; conveniently administered, for example, in divided doses up to four times a day.

The process of producing the above identified compounds is exemplified by the reaction scheme in FIG. 1. It is to be understood, that the reaction scheme is only a preferred example of the process for producing compounds according to the present invention.

For example, compound 11 can be obtained by esterification of clavulanic acid. Subsequently, according to method A1, compound 11 is oxidized with a suitable oxidant. One option of converting the hydroxyl group of compound 11 to an aldehyde group is the Dess Martin oxidation procedure using Dess Martin's periodinane reagent.

According to methods B1 to B3, compound 12 is reacted with a suitable nucleophilic agent to form compound 13. Method B1 preferably is a palladium catalyzed nucleophilic substitution reaction.

In method B2, 1,4-dibromobutene and $K_2CO_3$ preferably react with compound 12, whereby the substituted compound 13 is obtained. Subsequently, in method B3, the obtained product of method B2 may be converted into the corresponding azido derivative using preferably tetrabutyl ammonium azide as reagent.

For obtaining alcohol 14 compound 13 can be reduced with a suitable reducing agent. Said method C2 may be carried out using $NaBH_4$ as reducing agent. Optionally, in method E1 the ester group of alcohol 14 may be cleaved to form the corresponding carboxylic acid 15.

According to method C1, aldehyde 13 is oxidized with an appropriate oxidant, thereby forming carboxylic acid derivative 16. In a preferred embodiment carboxylic acid derivatives 16a and 16b may be formed as mixture of both E- and Z-isomers in the aforementioned oxidation reaction. If the substituent $R_6$ is hydrogen as in compound 16a the configuration of the double bond of the alkenyl moiety preferably is Z. It the substituent $R_7$ is hydrogen as in compound 16b, the product obtained is preferably only one of the possible E or Z-isomers.

In method E1 the ester group of the Z-isomer 16a is cleaved with an appropriate agent, thereby forming the dicarboxylic acid derivative 17. Compound 16b may optionally be converted to diester 18 by an appropriate esterification process (Method $F_1$, $R_9$ is as defined for $R_1$).

In method D1 the 5-membered ring of compound 19 is formed by reacting compound 16b with a suitable ring forming agent. In the ring forming reaction D1 the substituent $R_6$ of compound 16b preferably is an allyl or substituted allyl group. The cyclization reaction preferably is catalyzed with iodine, thereby forming compound 19 whereby R is an iodated alkyl or substituted alkyl group.

According to one method, compound 19 may be dehalogenated using preferably a palladium catalyzed dehalogenation reaction. Alternatively, according to another method, if R in compound 19 is an iodated alkyl or substituted alkyl group, said compound may be converted into the corresponding azido derivative.

Compound 20 may be obtained by cleaving the ester group of compound 19. Said cleaving reaction preferably is a reductive ester cleavage reaction. In case that R is an alkyl group substituted with an azido group, said azido group is preferably reduced as well simultaneously.

A person skilled in the art will recognize several alternatives of the described specific reactions with which the same reaction products may be obtained.

BRIEF DESCRIPTION OF THE DRAWINGS

FIG. 1 shows a preferred exemplified reaction scheme of a process for producing compounds of the present invention.

The invention will be illustrated by the following examples which, however, are not limitative.

EXAMPLES

All temperatures are in degrees Celsius (° C.) and are uncorrected. In the NMR spectra all chemical shift values are in ppm.

The following abbreviations are used: s: singlet; d: doublet; t: triplet; q: quartet; m: multiplet; dd: doublet of doublet; dt: doublet of triplet; dq: doublet of quartet; ddt: doublet of doublet of triplet; br: broad; ABq: AB quartet; DMSO: dimethyl sulfoxide; aq: aqueous; rt: room temperature.

Preparation of Intermediates (Starting Materials) for the Compounds of Examples 1-22

Example A

Mixture of (5R)-7-oxo-3-(2-oxo-ethylidene)-4-oxa-1-aza-bicyclo[3.2.0]heptane-2-carboxylic acid benzyl ester and (R)-3-(2-hydroxy-vinyl)-7-oxo-4-oxa-1-aza-bicyclo[3.2.0]hept-2-ene-2-carboxylic acid benzyl ester

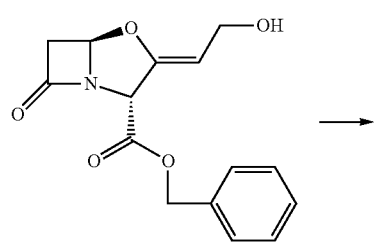

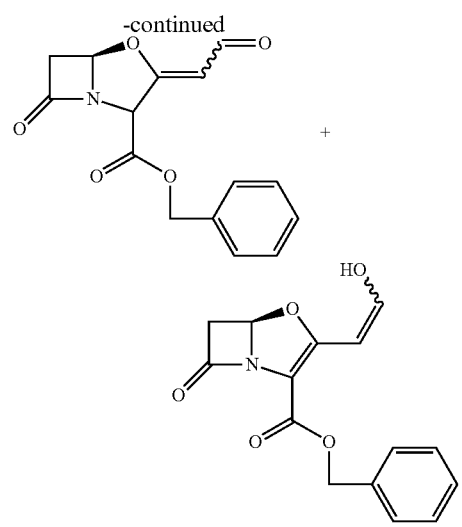

A mixture of (2R,5R)-3-[2-hydroxy-eth-(Z)-ylidene]-7-oxo-4-oxa-1-aza-bicyclo[3.2.0]heptane-2-carboxylic acid benzyl ester (58.86 g), 1200 ml of dry dichloromethane, 59 g of 4 Å molecular sieves and Dess Martin periodinane (1,1,1-tris(acetyloy)-1,1-dihydro-1,2-benziodoxol-3(1H)-one) (76.52 g) is stirred for 1.5 h at 0-5° C. and then for 40 min at 10° C. The mixture is filtered through a sintered funnel and the filtrate is poured into a 10 liter reactor containing a solution of 503.2 g of sodium thiosulfate.5H$_2$O dissolved in 2370 ml of saturated aq NaHCO$_3$ under mechanical stirring. Subsequently 600 ml of diethyl ether are added and the mixture is stirred for 20 min. 1500 ml of ethyl acetate and 500 ml of diethyl ether are added and stirred for a further 2 min. The aqueous phase is removed and the organic phase is washed twice with 600 ml aq. saturated NaHCO$_3$ each, twice with 600 ml brine each, dried (MgSO$_4$), filtered and stripped of the solvent at room temperature and under vacuum to give oil. The oil is chromatographed over an SiO$_2$ column using toluene/ethyl acetate (6/1) containing 0.05% acetic acid. The fractions containing the desired compound are combined and washed with 400 ml 5% aq NaHCO$_3$, twice with 400 ml brine each, dried and stripped of the solvents. The title compound is obtained as an oil, having characterization data as indicated below.

PatAZ9433h $^1$H-NMR (DMSO-d$_6$, 400 MHz): δ 11.07 (br. s); 9.84 (d, J=8.2 Hz); 9.59 (d, J=6.8 Hz); 7.41-7.32 (m); 6.33 (d, J=1.1 Hz); 6.10 (d, J=12.4 Hz); 6.07 (d, J=2.7 Hz); 5.99 (d, J=2.7 Hz); 5.96 (d, J=2.4 Hz); 5.88 (s); 5.83 (dd, J=6.9, 1.2 Hz); 5.35 (dd, J=8.2, 0.6 Hz); 5.23-5.18 (overlapping multiplets); 3.84-3.75 (overlapping multiplets); 3.49 (d, J=17.2 Hz); 3.41 (d, J=17.2 Hz); 3.35 (d, J=17.2 Hz).

Example B

Mixture of (5R)-7-oxo-3-(2-oxo-ethylidene)-4-oxa-1-aza-bicyclo[3.2.0]heptane-2-carboxylic acid methyl ester and (R)-3-(2-hydroxy-vinyl)-7-oxo-4-oxa-1-aza-bicyclo[3.2.0]hept-2-ene-2-carboxylic acid methyl ester

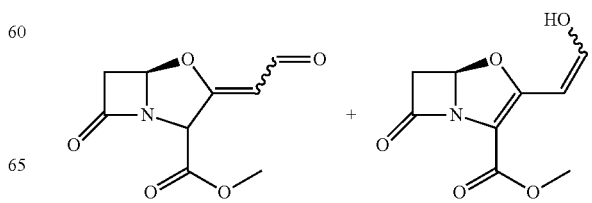

Analogously to the method described in Example A, but using (2R,5R)-3-[2-hydroxy-eth-(Z)-ylidene]-7-oxo-4-oxa-1-aza-bicyclo[3.2.0]heptane-2-carboxylic acid methyl ester, the title compound is obtained as an oil having characterization data as indicated below.

PatAZ8242I $^1$H-NMR (DMSO-$d_6$, 400 MHz): δ 11.01 (br. s); 9.85 (d, J=8.2 Hz); 9.58 (d, J=6.8 Hz); 7.34 (d, J=12.3 Hz); 6.24 (d, J=1.3 Hz); 6.10 (d, J=12.6 Hz); 6.07 (d, J=2.4 Hz); 5.99 (d, J=2.4 Hz); 5.95 (d, J=2.0 Hz); 5.83 (dd, J=1.3, 6.9 Hz); 5.80 (d, J=0.8 Hz); 5.36 (dd, J=0.9, 8.2 Hz); 3.81 & 3.77 (two overlapping doublet of doublets); 3.74 (s); 3.73 (s); 3.67 (s); 3.47 (d, J=17.2 Hz); 3.40 (d, J=17.2 Hz); 3.35 (d, J=17.2 Hz).

Example C

Mixture of (5R)-7-oxo-3-(2-oxo-ethylidene)-4-oxa-1-aza-bicyclo[3.2.0]heptane-2-carboxylic acid 2,2-dimethyl-propionyloxymethyl ester and (R)-3-(2-hydroxy-vinyl)-7-oxo-4-oxa-1-aza-bicyclo[3.2.0]hept-2-ene-2-carboxylic acid 2,2-dimethyl-propionyloxymethyl ester

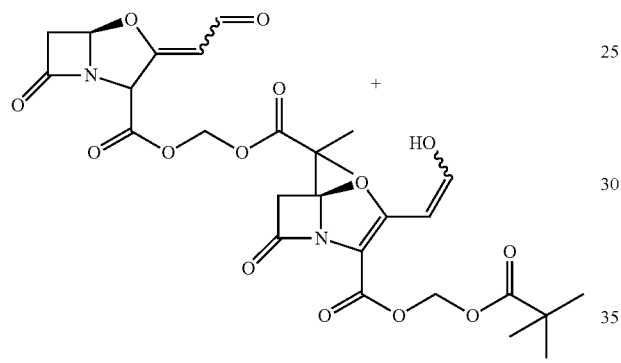

Analogously to the method described in Example A, but using (2R,5R)-3-[2-hydroxy-eth-(Z)-ylidene]-7-oxo-4-oxa-1-aza-bicyclo[3.2.0]heptane-2-carboxylic acid 2,2-dimethyl-propionyloxymethyl ester, the title compound is obtained as an oil having characterization data as indicated below.

PatAZ9481H $^1$H-NMR (DMSO-$d_6$, 400 MHz): δ 11.25 (br. s); 9.84 (d, J=7.9 Hz); 9.55 (d, J=6.6 Hz); 7.42 (d, J=12.1 Hz); 6.32 (d, J=1.3 Hz); 6.06 (d, J=12.4 Hz); 5.98-5.96 (overlapping multiplets); 5.91 (d, J=0.9 Hz); 3.84-3.76 (overlapping multiplets); 3.49 (d, J=17.2 Hz); 3.42 (d, J=17.2 Hz); 3.36 (d, J=17.2 Hz).

Example D

Benzyl-(4-bromo-but-2-enyl)-carbamic acid benzyl ester

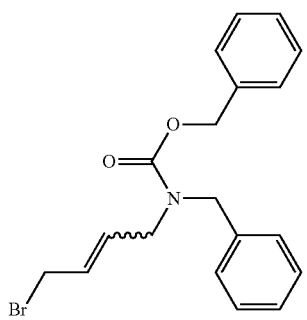 [SMILES: O=C(OCc1ccccc1)N(CC=CCBr)Cc1ccccc1]

A mixture of N-benzyloxycarbonylbenzylamine (50 g), 1,4-dibromo-2-butene (44 g) and NaH (10.7 g, 60% in oil) in 350 ml of DMF is stirred at 0° C. for 1 h and then at 25° C. for 3 h. The reaction mixture is subjected to aqueous workup and the residue obtained is purified by chromatography over SiO$_2$. The title compound is obtained as an oil having characterization data as indicated below.

Pat AZ 1840K $^1$H-NMR (400 MHz, DMSO): 7.42-7.16 (m, 10H); 5.79 (br s, 2H); 5.12 (s, 2H); 4.41 (s, 2H); 4.10 (br s); 3.85 (br s).

Examples 1, 2 and 3

Example 1

(5R)-3-(1-Formyl-but-3-enylidene)-7-oxo-4-oxa-1-aza-bicyclo[3.2.0]heptane-2-carboxylic acid benzyl ester

Example 2

(5R)-2-Allyl-7-oxo-3-[2-oxo-ethylidene]-4-oxa-1-aza-bicyclo[3.2.0]heptane-2-carboxylic acid benzyl ester

Example 3

(5R)-2-Allyl-3-[1-formyl-but-3-enylidene]-7-oxo-4-oxa-1-aza-bicyclo[3.2.0]heptane-2-carboxylic acid benzyl ester

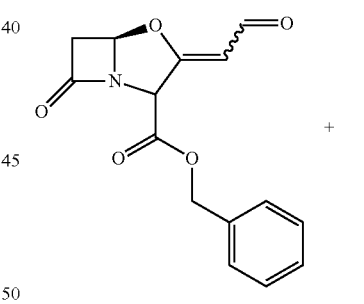

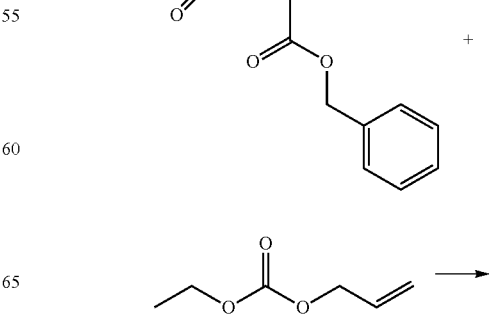

-continued

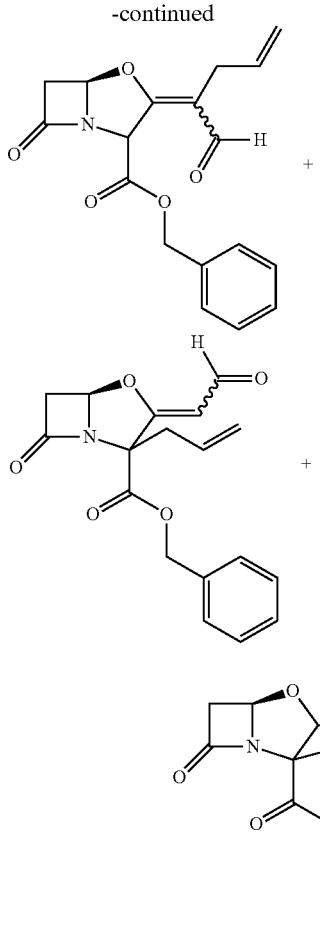

A mixture of compound of Example A (32.46 g), 500 ml of dichloromethane, carbonic acid allyl ester ethyl ester (11.13 ml) and Pd(Ph₃P)₄ (3.92 g) is stirred under argon atmosphere for 1 h 15 min. The solvent is removed under vacuum to obtain a residue. The residue is subjected to chromatography over an SiO₂ column using toluene/t-butyl methyl ether (25/1, 20/1 and 15/1). The compound of Example 1 is obtained as an oil, having characterization data as indicated below.

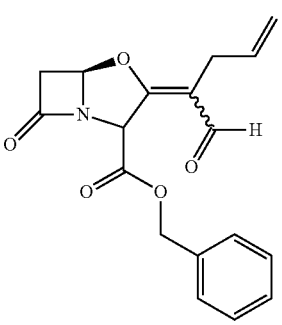

PatAZ2506i ¹H-NMR (DMSO-d₆, 400 MHz): δ 9.62 (s, 1H); 7.40-7.32 (m, 5H); 6.47 (s, 1H); 6.00 (dd, J=3.1, 0.7 Hz; 1H); 5.77-5.68 (m, 1H); 5.20 and 5.23 (two doublets as ABq, J=12.6 Hz, 2H); 4.93-4.87 (m, 2H); 3.78 (dd, J=3.1, 17.2 Hz, 1H); 3.30 (dd, J=17.2, 0.7 Hz, 1H); 2.95 (dt, Jd=6.0 Hz, Jt=1.4 Hz, 2H).

The compound of Example 2 is obtained as an oil, having characterization data as indicated below.

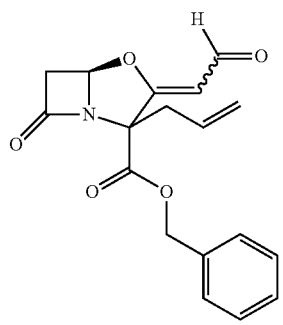

PatAZ 02505i ¹H-NMR (DMSO-d₆, 400 MHz): mixture of isomers;

Data of major isomer: δ 9.84 (d, J=7.8 Hz, 1H); 7.40-7.30 (m, 5H); 5.94 (d, J=2.8 Hz, 1H); 5.76-5.67 (m, 1H); 5.45 (d, J=8.0 Hz, 1H); 5.22-5.16 (overlapping multiplets); 3.70 (dd, J=2.9, 17.0 Hz; 1H); 3.41 (d, J=17.0 Hz, 1H); 3.10 (dd, J=8.5, 14.6 Hz, 1H);

Data of minor isomer: δ 9.86 (d, J=8.0 Hz, 1H); 7.40-7.30 (m, 5H); 5.92 (d, J=2.6 Hz, 1H); 5.90-5.85 (m, 1H); 5.36 (d, J=7.9 Hz, 1H); 5.26 (d, J=12.4 Hz, 1H); 5.22-5.16 (overlapping multiplets); 5.10 (d, J=12.5 Hz, 1H); 3.64 (dd, J=2.9, 17.0 Hz); 3.40 (d, J=17.1 Hz); 2.70 (dd, J=7.1, 14.2 Hz).

The compound of Example 3 is obtained as a foam, having characterization data as indicated below.

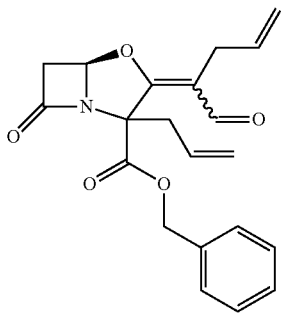

PatAZ02523i ¹H-NMR (DMSO-d₆, 500 MHz): δ 9.69 (s, 1H); 7.38-7.31 (m, 5H); 5.81 (d, J=2.3 Hz, 1H); 5.73-5.63 (m, 2H); 5.21 & 5.24 (two doublets as ABq, J=12.4 Hz, 2H); 5.18 (dd, J=1.8, 16.9 Hz, 1H); 5.13 (dd, J=1.8, 10.1 Hz, 1H); 4.88 (dq, Jd=6.0, Jq=1.6 Hz, 1H); 4.86 (t, J=1.6 Hz, 1H); 3.62 (dd, J=2.8, 17.0 Hz, 1H); 3.53 (ddt, Jd=6.4, 15.1, Jt=1.4 Hz, 1H); 3.42 (dd, J=0.9, 16.9 Hz, 1H); 3.18 (dd, J=7.3, 15.6 Hz, 1H); 2.98 (ddt, Jd=6.0, 15.1, Jt=1.4 Hz, 1H); 2.93 (ddt, Jd=6.0, 15.1, Jt=1.4 Hz, 1H).

Examples 4, 5 and 6

Example 4

(5R)-3-[1-Formyl-4-phenyl-but-3-enylidene]-7-oxo-4-oxa-1-aza-bicyclo[3.2.0]heptane-2-carboxylic acid benzyl ester Example 5

(5R)-7-oxo-3-[2-oxo-ethylidene]-2-(3-phenyl-allyl)-4-oxa-1-aza-bicyclo[3.2.0]heptane-2-carboxylic acid benzyl ester

Example 6

Isomer of Compound of Example 5

(5R)-7-oxo-3-[2-oxo-ethylidene]-2-(3-phenyl-allyl)-4-oxa-1-aza-bicyclo[3.2.0]heptane-2-carboxylic acid benzyl ester Analogously to the method described in Examples 1-3, but using the compound of Example A and carbonic acid ethyl ester (E)-3-phenyl-allyl ester, the compound of Example 4 as an oil, having characterization data as indicated below

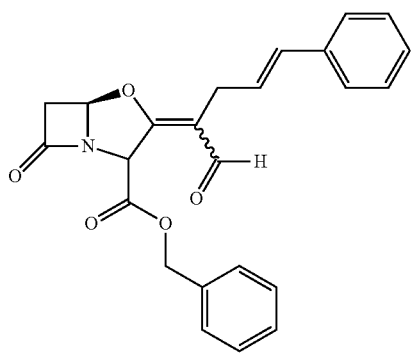

PatAZ2588i $^1$H-NMR (DMSO-$d_6$, 400 MHz): δ 9.66 (s, 1H); 7.40-7.20 (m, 10H); 6.50 (s, 1H); 6.32 (d, J=15.8 Hz, 1H); 6.17 (dt, Jd=15.8, Jt=6.3 Hz; 1H); 6.04 (d, J=2.5 Hz, 1H); 5.24 & 5.20 (two doublets as ABq, J=12.4 Hz, 2H); 3.78 (dd, J=3.1, 17.2 Hz, 1H); 3.31 (d, J=17.1 Hz, 1H); 3.12 (d, J=6.2 Hz, 2H);

as well as the compound of Example 5 as an oil, having characterization data as indicated below

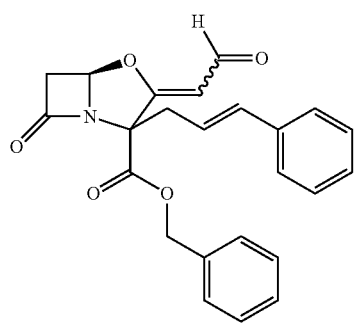

PatAZ2590i $^1$H-NMR (DMSO-$d_6$, 400 MHz): δ 9.87 (d, J=7.8 Hz, 1H); 7.35-7.20 (m, 10H); 6.56 (d, J=15.9 Hz, 1H); 6.29 (ddd, J=15.9, 8.4, 5.6 Hz, 1H); 5.97 (d, J=2.3 Hz, 1H); 5.52 (d, J=7.9 Hz, 1H); 5.18 (s, 2H); 3.72 (dd, J=3.1, 17.0 Hz, 2H); 3.44 (d, J=17.1 Hz, 1H); 3.31 (dd, J=14.9, 8.6 Hz, 1H); 3.03 (ddd, J=14.5, 5.6, 1.4 Hz, 1H);

as well as the compound of Example 6 as an oil, having characterization data as indicated below

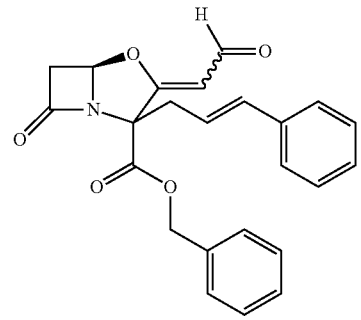

PatAZ2589i $^1$H-NMR (DMSO-$d_6$, 400 MHz): δ 9.86 (d, J=7.9 Hz, 1H); 7.40-7.20 (m, 10H); 6.55 (d, J=15.9 Hz, 1H); 6.15 (dt, Jd=15.6, Jt=7.5, 1H); 5.92 (d, J=2.0 Hz, 1H); 5.40 (d, J=7.9 Hz, 1H); 5.29 (d, J=12.6 Hz, 1H); 5.15 (d, J=12.4 Hz, 1H); 3.64 (dd, J=3.0, 17.1 Hz, 1H); 3.40 (dd, J=0.7, 17.2 Hz, 1H); 3.02 (ddd, J=1.1, 7.3, 16.4 Hz, 1H); (2.88, ddd, J=1.1, 7.3, 16.4 Hz, 1H);
are obtained.

Examples 7, 8 and 9

Example 7

(5R)-3-[1-Formyl-5-hydroxy-pent-3-enylidene]-7-oxo-4-oxa-1-aza-bicyclo[3.2.0]heptane-2-carboxylic acid benzyl ester

Example 8

(5R)-2-(4-Hydroxy-but-2-enyl)-7-oxo-3-[2-oxo-ethylidene]-4-oxa-1-aza-bicyclo[3.2.0]heptane-2-carboxylic acid benzyl ester

Example 9

Isomer of Compound of Example 8

(5R)-2-(4-Hydroxy-but-2-enyl)-7-oxo-3-[2-oxo-ethylidene]-4-oxa-1-aza-bicyclo[3.2.0]heptane-2-carboxylic acid benzyl ester Analogously to the method described in Examples 1-3, but using the compound of Example A and 4-Vinyl-[1,3]dioxolan-2-one, the compound of Example 7 as an oil, having characterization data as indicated below

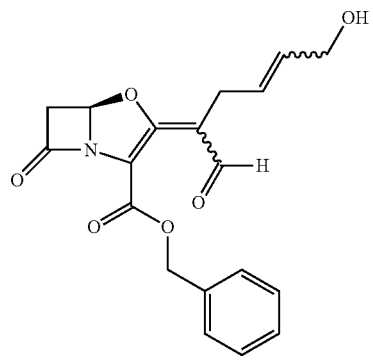

PatAZ2574i $^1$H-NMR (DMSO-d$_6$, 400 MHz): δ 9.61 (s, 1H); 7.40-7.33 (m, 5H); 6.44 (s, 1H); 6.00 (d, J=2.4, 1H); 5.54-5.39 (m, 2H); 5.23 and 5.19 (two doublets as ABq, J=12.4 Hz, 2H); 4.57 (t, J=5.5 Hz, 1H); 3.82 (br. m, 2H); 3.78 (dd, J=2.9, 17.0 Hz, 1H); 3.30 (d, J=16.8 Hz, 1H); 2.93 (br. d, J=4.0 Hz, 2H);

the compound of Example 8 as an oil, having characterization data as indicated below

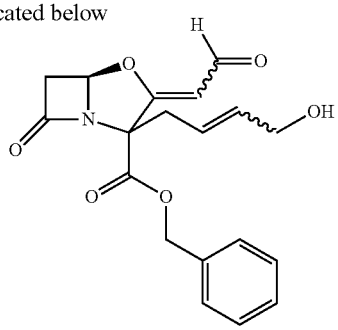

Pat AZ2530i, $^1$H-NMR (DMSO-d$_6$, 400 MHz): δ 9.87 (d, J=7.9 Hz, 1H); 7.41-7.32 (m, 5H); 5.90 (d, J=2.3 Hz, 1H); 5.76-5.70 (m, 1H); 5.50 (dt, Jd=15.5, Jt=7.3 Hz, 1H); 5.36 (d, J=7.9 Hz, 1H); 5.26 (d, J=12.4 Hz, 1H); 5.10 (d, J=12.5 Hz, 1H); 4.70 (t, J=5.5 Hz, 1H); 3.89 (t, J=4.6 Hz, 2H); 3.64 (dd, J=2.8, 17.0 Hz, 1H); 3.38 (d, J=17.1 Hz, 1H); 2.82 (dd, J=7.5, 14.1 Hz, 1H); 2.68 (dd, J=14.4, 6.7 Hz, 1H);

and the compound of Example 9 as an oil, having characterization data as indicated below

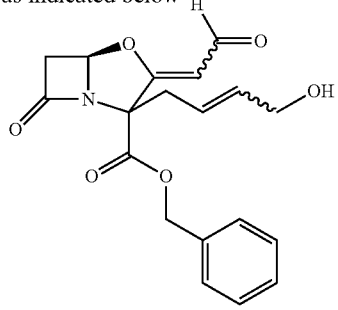

PatAZ2570i, $^1$H-NMR (DMSO-d$_6$, 400 MHz): δ 9.84 (d, J=7.9 Hz, 1H); 7.40-7.32 (m, 5H); 5.93 (d, J=2.5 Hz, 1H); 5.72-5.69 (m, 2H); 5.45 (d, J=8.0 Hz, 1H); 5.18 (s, 2H); 4.70 (t, J=5.4 Hz, 1H); 3.84-3.80 (br. m, 2H); 3.69 (dd, J=2.9, 16.9 Hz, 1H); 3.40 (d, J=16.9 Hz, 1H); 3.13-3.05 (m, 1H); 2.85-2.79 (m, 1H);

are obtained.

Examples 10, 11 and 12

Example 10

(5R)-3-[5-Acetoxy-1-formyl-pent-3-enylidene]-7-oxo-4-oxa-1-aza-bicyclo[3.2.0]heptane-2-carboxylic acid benzyl ester Example 11

(5R)-2-(4-Acetoxy-but-2-enyl)-7-oxo-3-[2-oxo-ethylidene]-4-oxa-1-aza-bicyclo[3.2.0]heptane-2-carboxylic acid benzyl ester Example 12

Isomer of Compound of Example 11

(5R)-2-(4-Acetoxy-but-2-enyl)-7-oxo-3-[2-oxo-ethylidene]-4-oxa-1-aza-bicyclo[3.2.0]heptane-2-carboxylic acid benzyl ester Analogously to the method as described in Examples 1-3, but using the compound of Example A and acetic acid 4-ethoxycarbonyloxy-but-2-enyl ester, the compound of Example 10 as an oil, having characterization data as indicated below

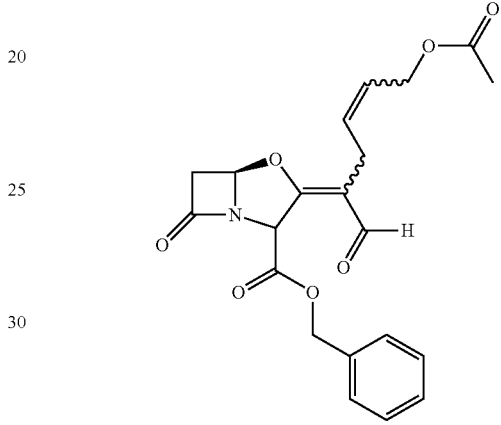

PatAZ 02579 I, $^1$H-NMR (DMSO-d$_6$, 400 MHz): mixture of isomers: δ 9.61 (s, 1H); 7.45-7.23 (m, 5H); 6.47 (s, 1H); 6.02 (d, J=2.3 Hz, 1H); 5.23 & 5.19 (two doublets as ABq, J=12.6 Hz, 2H); 3.79 (dd, J=2.4, 17.2 Hz, 1H); 3.30 (d overlapping with other signals, J=16.8 Hz, 1H); 2.96 (ABx m, J(AB)=15.4, J(Ax)=J(Bx)=5.3 Hz, 2H); 1.98 (s, 3H);

as well as the compound of Example 11 as an oil, having characterization data as indicated below

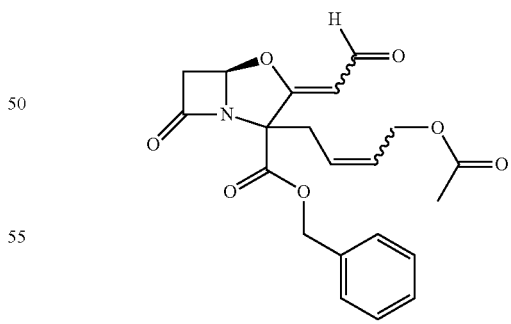

PatAZ2580i, $^1$H-NMR (DMSO-d$_6$, 400 MHz): δ 9.84 (d, J=7.7 Hz, 1H); 7.40-7.37 (br. s, 5H); 5.95 (d, J=2.0 Hz, 1H); 5.83 (ddd, J=5.9, 7.7, 14.8 Hz, 1H); 5.71 (dt, Jd=15.4, Jt=5.7 Hz, 1H); 5.46 (d, J=7.9 Hz, 1H); 5.19 (s, 2H); 4.39 (d, J=5.7 Hz, 2H); 3.70 (dd, J=2.2, 16.9 Hz, 1H); 3.41 (d, J=16.8 Hz, 1H); 3.15 (dd, J=8.4, 14.6 Hz, 1H); 2.85 (dd, J=4.8, 14.4 Hz, 1H); 1.99 (s, 3H);

and the compound of Example 12 as an oil, having characterization data as indicated below

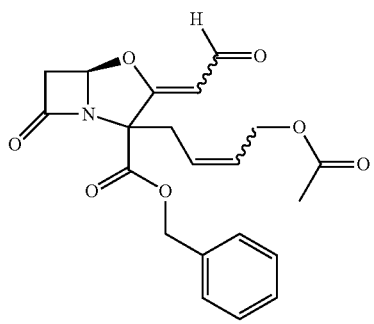

PatAZ 2581i $^1$H-NMR (DMSO-$d_6$, 400 MHz): δ 9.85 (d, J=7.9 Hz, 1H); 7.40-7.33 (br. s, 5H); 5.90 (br. s, 1H); 5.75-5.62 (m, 2H); 5.37 (d, J=7.9 Hz, 1H); 5.27 & 5.11 (two doublets as ABq, J=12.4 Hz, 2H); 4.47 (d, J=5.3 Hz, 2H); 3.66 (dd, J=2.0, 17.0 Hz, 1H); 3.40 (d, J=17.2 Hz, 1H); 2.85 (dd, J=6.3, 14.2 Hz, 1H); 2.72 (dd, J=6.3, 14.2 Hz, 1H); 2.0 (s, 3H);
are obtained.

Examples 13, 14 and 15

Example 13

(5R)-3-((1-Formyl-4-phenyl-but-3-enylidene)-7-oxo-4-oxa-1-aza-bicyclo[3.2.0]heptane-2-carboxylic acid methyl ester Example 14

(5R)-7-oxo-3-[2-oxo-ethylidene]-2-(3-phenyl-allyl)-4-oxa-1-aza-bicyclo[3.2.0]heptane-2-carboxylic acid methyl ester Example 15

Isomer of Compound of Example 14

(5R)-7-oxo-3-[2-oxo-ethylidene]-2-(3-phenyl-allyl)-4-oxa-1-aza-bicyclo[3.2.0]heptane-2-carboxylic acid methyl ester Analogously to the method described in Examples 1-3, but using the compound of Example B and carbonic acid ethyl ester (E)-3-phenyl-allyl ester, the compound of Example 13 as an oil, having characterization data as indicated below

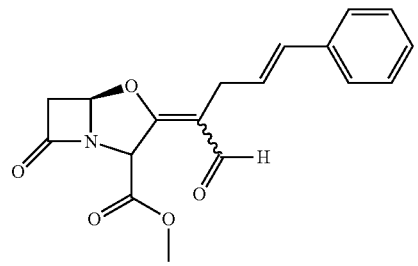

PatAZ8256i $^1$H-NMR (DMSO-$d_6$, 400 MHz): δ 9.65 (s, 1H); 7.35-7.15 (m, 5H); 6.42 (s, 1H); 6.33 (d, J=16.1 Hz, 1H); 6.21 (dt, Jd=15.9, Jt=6.1 Hz, 1H); 6.04 (d, J=2.4 Hz, 1H); 3.78 (dd, J=17.2, 3.0 Hz, 1H); 3.74 (s, 3H); 3.32 (d, J=17.2 Hz, 1H); 3.14 (d, J=6.0 Hz, 2H);
as well as the compound of Example 14 as a foam, having characterization data as indicated below

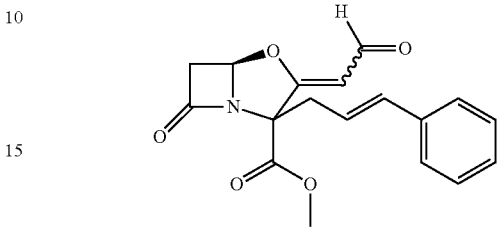

PatAZ8273i $^1$H-NMR (DMSO-$d_6$, 400 MHz): δ 9.87 (d, J=8.0 Hz, 1H); 7.38-7.22 (m, 5H); 6.62 (d, J=15.8 Hz, 1H); 6.33 (ddd, J=5.7, 8.6, 15.9 Hz, 1H); 5.98 (d, J=2.5 Hz, 1H); 5.50 (d, J=8.0 Hz, 1H); 3.72 (dd, J=2.8, 17.0 Hz, 1H); 3.72 (s, 3H); 3.45 (d, J=17.0 Hz, 1H); 3.28 (dd, J=8.5, 14.7 Hz, 1H); 3.02 (ddd, J=1.3, 5.6, 14.7 Hz, 1H);
and the compound of Example 15 as a foam, having characterization data as indicated below

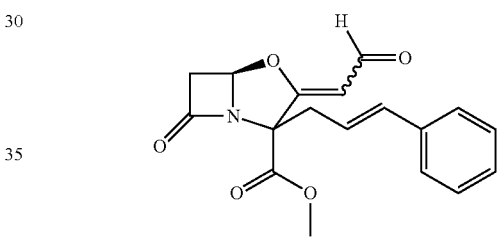

PatAZ8271i $^1$H-NMR (DMSO-$d_6$, 400 MHz): δ 9.88 (d, J=8.0 Hz, 1H); 7.44-7.22 (m, 5H); 6.57 (d, J=15.8 Hz, 1H); 6.17 (dt, Jd=15.7, Jt=7.5 Hz, 1H); 5.89 (d, J=2.2 Hz, 1H); 5.43 (d, J=7.9 Hz, 1H); 3.75 (s, 3H); 3.63 (dd, J=2.9, 16.9 Hz, 1H); 3.44 (d, J=17.2 Hz, 1H); 3.00 (dd, J=7.9, 14.1 Hz, 1H); 2.85 (ddd, J=1.0, 7.3, 14.3 Hz, 1H);
are obtained.

Examples 16 and 17

Example 16

(5R)-3-[1-Formyl-but-3-enylidene]-7-oxo-4-oxa-1-aza-bicyclo[3.2.0]heptane-2-carboxylic acid methyl ester Example 17

(5R)-2-Allyl-7-oxo-3-[2-oxo-ethylidene]-4-oxa-1-aza-bicyclo[3.2.0]heptane-2-carboxylic acid methyl ester Analogously to the method as described in Examples 1-3, but using the compound of Example B and carbonic acid allyl ester ethyl ester, the compound of Example 16 as an oil, having characterization data as indicated below

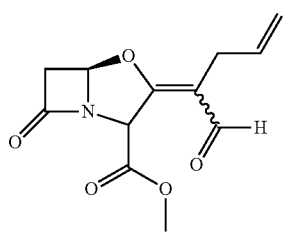

PatAZ8277i ¹H-NMR (DMSO-d₆, 400 MHz): 9.60 (s, 1H); 6.39 (s, 1H); 6.00 (d, J=2.7 Hz, 1H); 5.81-5.71 (m, 1H); 4.94 (dd, J=16.6, 1.7 Hz, 1H); 4.93 (dd, J=10.6, 1.7 Hz, 1H); 3.78 (dd, J=17.2, 3.1 Hz, 1H); 3.27 (d, J=17.4 Hz, 1H); 2.96 (d, J=6.0 Hz, 2H);

as well as the compound of Example 17 as an oil, having characterization data as indicated below

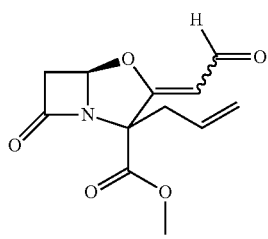

PatAZ8278i ¹H-NMR (DMSO-d₆, 400 MHz): mixture of isomers

Data of major isomer: δ 9.85 (d, J=7.7 Hz, 1H); 5.45 (d, J=7.9 Hz, 1H); 5.22-5.18 (br. m, 2H); 3.71 (s, 3H); 3.42 (d, J=17.0 Hz, 1H); 3.10 (dd, J=8.5, 14.7 Hz, 1H);

Data of minor isomer: δ 9.87 (d, J=7.7 Hz, 1H); 5.38 (d, J=7.9 Hz, 1H); 5.28-5.23 (br. m, 2H); 3.72 (s, 3H); 3.64 (dd, J=2.9, 17.0 Hz, 1H); 3.44 (dd, J=17.0, 0.8 Hz, 1H); 2.67 (dd, J=7.1, 14.1 Hz, 1H);

are obtained.

Examples 18 and 19

Example 18

(5R)-3-[1-Formyl-4-phenyl-but-3-enylidene]-7-oxo-4-oxa-1-aza-bicyclo[3.2.0]heptane-2-carboxylic acid 2,2-dimethyl-propionyloxymethyl ester Example 19

(5R)-7-oxo-3-(2-oxo-ethylidene)-2-(3-phenyl-allyl)-4-oxa-1-aza-bicyclo[3.2.0]heptane-2-carboxylic acid 2,2-dimethyl-propionyloxymethyl ester Analogously to the method as described in Examples 1-3, but using the compound of Example C and carbonic acid ethyl ester (E)-3-phenyl-allyl ester, the compound of Example 18 as oil, having characterization data as indicated below

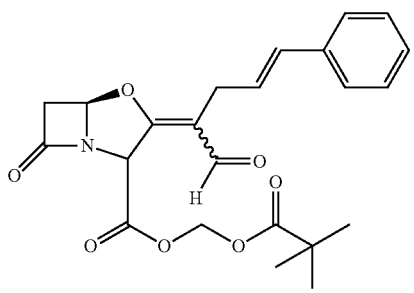

PatAZ9488H ¹H-NMR (DMSO-d₆, 400 MHz): δ 9.61 (s, 1H); 7.35-7.17 (m, 5H); 6.50 (s, 1H); 6.34 (d, J=15.9 Hz, 1H); 6.18 (dt, Jd=15.9, Jt=6.3 Hz, 1H); 6.02 (d, J=2.4 Hz, 1H); 5.82 & 5.77 (two doublets as ABq, J=5.8 Hz, 2H); 3.81 (dd, J=3.1, 17.2 Hz, 1H); 3.35 (dd, J=17.2, 0.6 Hz, 1H); 3.12 (dd, J=6.4, 0.9 Hz, 2H); 1.08 (br. s, 9H);

as well as the compound of Example 19 as an oil, having characterization data as indicated below

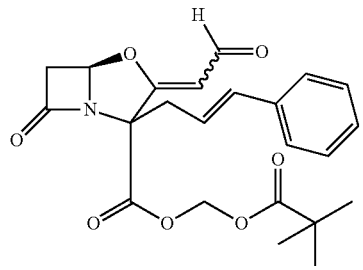

PatAZ9487H ¹H-NMR (DMSO-d₆, 400 MHz): mixture of isomers:

Data of major isomer: δ 9.86 (d, J=7.7 Hz, 1H); 7.42-7.14 (several multiplets, 5H); 6.65 (d, J=16.1 Hz, 1H); 6.33 (ddd, J=5.7, 8.4, 15.9 Hz, 1H); 5.95 (d, J=2.2 Hz, 1H); 5.80 & 5.78 (two doublets as ABq, J=6.0 Hz, 2H); 5.47 (d, J=7.9 Hz, 1H); 3.74 (dd, J=3.1, 17.0 Hz, 1H); 3.47 (d, J=17.0 Hz, 1H); 1.02 (s, 9H);

Data of minor isomer: δ 9.87 (d, J=7.9 Hz, 1H); 7.42-7.14 (several multiplets, 5H); 6.58 (d, J=15.9 Hz, 1H); 6.15 (dt, Jd=15.9, Jt=7.5 Hz, 1H); 5.93 (dd, J=2.9, 0.7 Hz, 1H); 5.88 & 5.84 (two doublets as ABq, J=5.2 Hz, 2H); 5.32 (d, J=7.9 Hz, 1H); 3.64 (dd, J=3.0, 17.0 Hz, 1H); 3.42 (d overlapping with other signals, J=17.0 Hz, 1H); 1.13 (s, 9H);

are obtained.

Example 20

(5R)-3-(5-Bromo-1-formyl-pent-3-enylidene)-7-oxo-4-oxa-1-aza-bicyclo[3.2.0]heptane-2-carboxylic acid benzyl ester

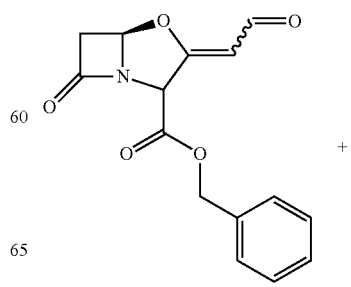

19

-continued

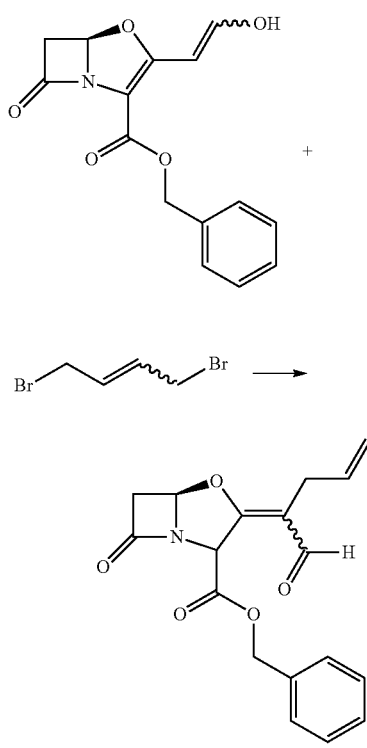

A mixture of compound of Example A (30.7 g), 160 ml dimethyl formamide, K$_2$CO$_3$ (6.6 g) and 1,4-dibromo-but-2-ene (20.57 g) is stirred under argon at 0-5° C. for 4 h. The mixture is partitioned between 1 liter of ethyl acetate and 1 liter of water containing KHSO$_4$ (14.5 g). The organic phase is separated, washed with brine, dried (MgSO$_4$) and stripped of the solvents to obtain a residue. The residue is subjected to chromatography over an SiO$_2$-column using toluene/ethyl acetate (12/1). The title compound is obtained as an oil, having characterization data as indicated below.

PatAZ1828k $^1$H-NMR (DMSO-d$_6$, 400 MHz): mixture of isomers; data of main isomer: δ 9.61 (s, 1H); 7.46-7.29 (m, 5H); 6.48 (s, 1H); 6.01 (d, J=2.7 Hz, 1H); 5.75 (dt as quintet, Jd=15.2, Jt=6.0 Hz, 1H); 5.58 (dt as quintet, Jd=15.0, Jt=7.6 Hz, 1H); 5.23 & 5.19 (two doublets as ABq, J ca. 12 Hz, 2H); 4.06 (d, J=7.5 Hz, 2H); 3.79 (dd, J=17.1, 3.0 Hz, 1H); 3.31 (d buried under H$_2$O signal); 3.04-2.91 (m, 2H).

Examples 21 and 22

Example 21

(5R)-3-[5-(Benzyl-benzyloxycarbonyl-amino)-1-formyl-pent-3-enylidene]-7-oxo-4-oxa-1-aza-bicyclo[3.2.0]heptane-2-carboxylic acid benzyl ester Example 22

(5R)-2-[4-(Benzyl-benzyloxycarbonyl-amino)-but-2-enyl]-7-oxo-3-[2-oxo-ethylidene]-4-oxa-1-aza-bicyclo[3.2.0]heptane-2-carboxylic acid benzyl ester Analogously to the method as described in Example 20, but using the compound of Example A and the compound of

20

Example D, the compound of Example 21 as an oil, having characterization data as indicated below

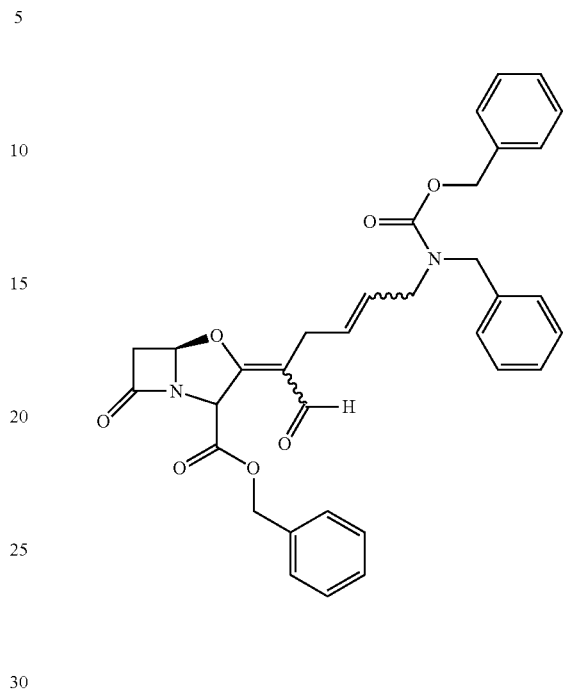

PatAZ1834k $^1$H-NMR (DMSO-d$_6$, 400 MHz): δ 9.60 (s, 1H); 7.41-7.29 (m, 15H), 6.45 (s, 1H); 5.97 (d, J=2.7 Hz, 1H); 5.52-5.09 (overlapping multiplets, 6H); 4.33 (s, 2H); 3.78 (dd, J=17.2, 3.1 Hz, 1H); 3.74-3.70 (br. d, 2H); 3.28-3.19 (br. d, 1H); 2.92 (d, J=5.5 Hz, 2H);

as well as the compound of Example 22 as an oil, having characterization data as indicated below

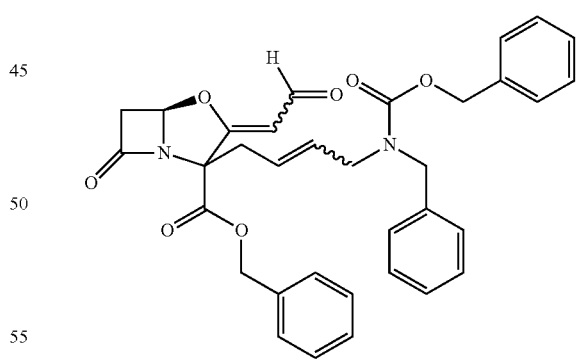

PatAZ1835k (DMSO-d$_6$, 400 MHz): mixture of isomers; data of major isomer: δ 9.84 (d, J=7.9 Hz, 1H); 7.40-7.14 (m, 15H); 5.57 (dt, Jd=15.2, Jt=5.8 Hz, 1H); 5.25 (d, J=12.4 Hz, 1H); 5.10 (s, 2H); 5.09 (d, J=12.1 Hz, 1H); 4.36 (br. m, 2H); 3.57 (br. dd, J=17.0, 2.2 Hz, 1H); 3.37 (br. d, 1H); 2.86-2.59 (two br. multiplets, 2H);

are obtained.

Example 23

(5R)-3-(5-Azido-1-formyl-pent-3-enylidene)-7-oxo-4-oxa-1-aza-bicyclo[3.2.0]heptane-2-carboxylic acid benzyl ester

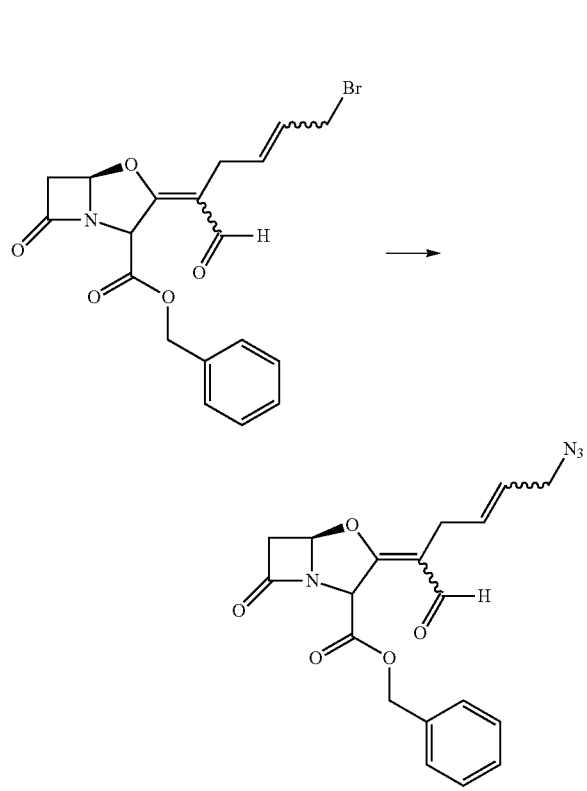

To an ice-cold mixture of the compound of Example 20 (900 mg) and 15 ml of tetrahydrofuran is added under stirring a solution of tetrabutyl ammonium azide (730 mg) in 15 ml of tetrahydrofuran in one portion and stirring is continued at 0-5° C. for 55 min. The mixture is partitioned between 350 ml of ethyl acetate and 350 ml of brine. The organic phase is separated and washed with 350 ml brine, dried (MgSO$_4$) and stripped of the solvents to obtain a mixture which is subjected to chromatography over SiO$_2$ using toluene/ethyl acetate (8/1). The title compound is obtained as an oil, having characterization data as indicated below PatAZ1849k $^1$H-NMR (DMSO-d$_6$, 400 MHz): mixture of isomers; data of major isomer: δ 9.62 (s, 1H); 7.37-7.32 (m, 5H); 6.47 (s, 1H); 6.00 (d, J=2.7 Hz, 1H); 5.74-5.67 (m, 1H); 5.43 (dtt, Jd=15.2, Jt=6.6, 1.3 Hz, 1H); 5.26-5.16 (overlapping multiplets, 2H); 3.79 (dd, J=3.0, 17.2 Hz, 1H); 3.73 (d, J=6.6 Hz, 2H); 3.29 (d, partly buried under H$_2$O signal, 1H); 2.98 (d, J=6.0 Hz, 2H).

Examples 24 and 25

Example 24

(5R)-3-(1-Carboxy-but-3-enylidene)-7-oxo-4-oxa-1-aza-bicyclo[3.2.0]heptane-2-carboxylic acid benzyl ester

Example 25

(5R)-2-Allyl-3-[1-carboxy-methylidene]-7-oxo-4-oxa-1-aza-bicyclo[3.2.0]heptane-2-carboxylic acid benzyl ester

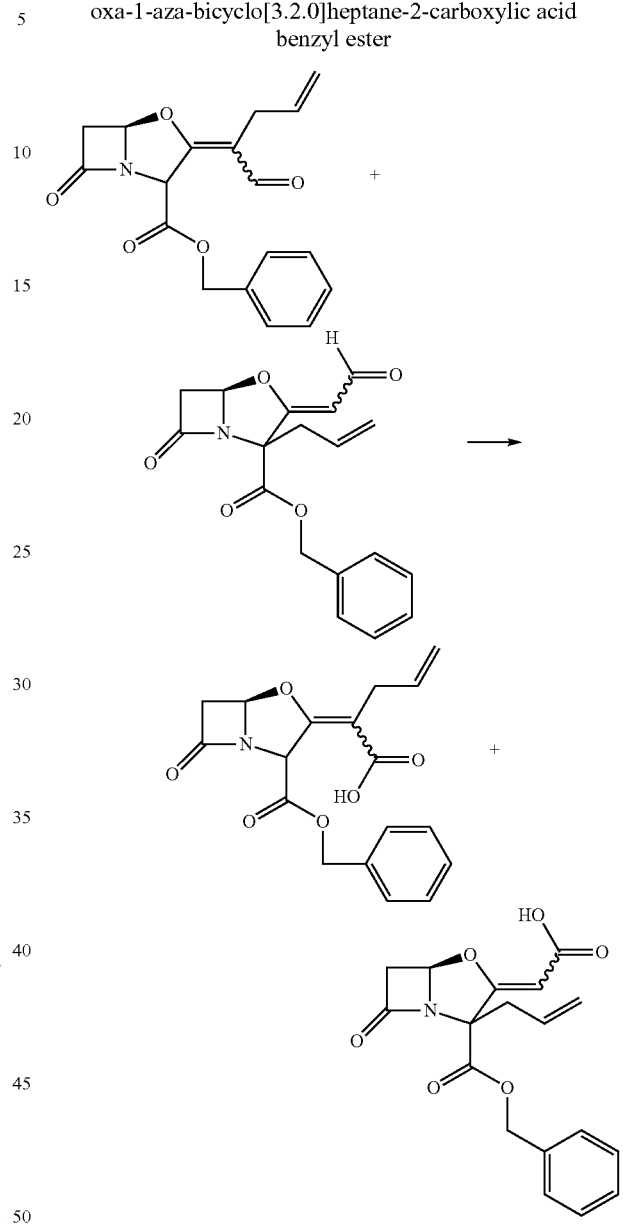

To a mixture of the compound of Example 1 and compound of Example 2 (37.76 g) are added 1130 ml of t-butanol, 370 ml of tetrahydrofuran and 2-methyl-2-butene (49.5 ml). The mixture is stirred at room temperature for 15 minutes, then cooled to 0-5° C., and cold aqueous 1M NaH$_2$PO$_4$ (475.8 ml) is added in one portion, followed by NaClO$_2$ (39.12 g) in 3 portions in intervals of 5 minutes. After stirring for 45 min at 0-5° C., the ice-bath is removed and stirring is continued at room temperature. After a total reaction time of 3.5 hours the solvents are removed under vacuum to obtain a suspension. 380 ml of ethyl acetate, 476 ml of cold aqueous 1M NaH$_2$PO$_4$ are added. The organic phase is separated and the aqueous phase is acidified with 159 ml of cold 1M NaH$_2$PO$_4$ and extracted with 380 ml of ethyl acetate. This acidification and extraction of the aqueous phase is repeated again. The combined organic extracts are dried (MgSO$_4$) and stripped of the solvents to obtain a mixture which is subjected to chromatography over an SiO$_2$ column using toluene/methyl t-butyl ether (15/1, 5/1 and 1/3). The compound of Example 24 as an oil, having characterization data as indicated below

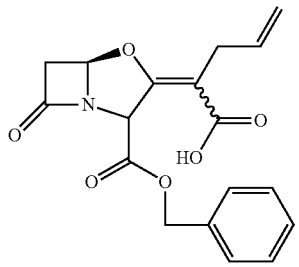

PatAZ8288i $^1$H-NMR (DMSO-d$_6$, 400 MHz): δ 12.7-12.4 (br. s, 1H); 7.41-7.31 (m, 5H); 5.88 (d, J=2.4, 1H); 5.79 (ddt, Jd=17.1, 10.1, Jt=5.9 Hz, 1H); 5.55 (s, 1H); 5.16 (s, 2H); 4.99 (dq, Jd=17.2, Jq=1.7 Hz, 1H); 4.91 (dq, Jd=10.1, Jq=1.1 Hz, 1H); 3.72 (dd, J=3.0, 17.1 Hz, 1H); 3.26 (d, J=17.0 Hz, 1H); 3.01 (d, J=6.0 Hz, 2H);

and the compound of Example 25 as an oil, having characterization data as indicated below

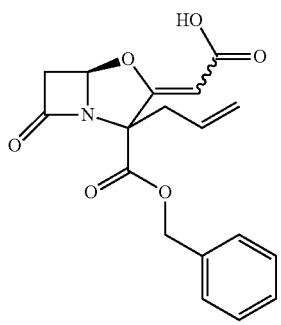

PatAZ7208K $^1$H-NMR (DMSO-d$_6$, 500 MHz): mixture of isomers; δ 11.99 (br. s, 1H); 7.39-7.33 (m, 5H); 5.94-5.86 (m, 0.6H); 5.84 (d, J=2.7 Hz, 0.6H); 5.80 (d, J=2.2 Hz, 0.4H); 5.75-5.66 (m, 0.4H); 5.26 (d, J=12.6 Hz, 0.4H); 5.23-5.12 (overlapping multiplets); 5.10 (s, 0.6H); 4.96 (s, 0.4H); 3.66 (dd, J=17.0, 2.7 Hz, 0.6H); 3.57 (dd, J=17.0, 2.7 Hz, 0.4H); 3.29 (d, J=17.0 Hz, 0.4H); 3.28 (d, J=17.0 Hz, 0.6H); 3.07 (dd, J=14.3, 8.8 Hz, 0.6H); 2.83-2.78 (m, 1H); 2.65 (dd, J=14.3, 7.1 Hz, 0.4H);

are obtained.

Example 26

(5R)-3-[1-Carboxy-4-phenyl-but-3-enylidene]-7-oxo-4-oxa-1-aza-bicyclo[3.2.0]heptane-2-carboxylic acid benzyl ester Analogously to the method described in Examples 24, 25, but using the compound of Example 4, the title compound is obtained as a syrup, having characterization data as indicated below.

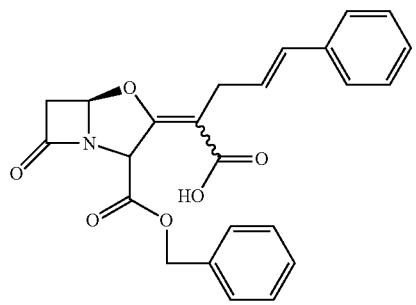

PatAZ9499h $^1$H-NMR (DMSO-d$_6$, 400 MHz): δ 12.62 (br. s, 1H); 7.36-7.28 (m, 10H); 6.37 (d, J=16.1 Hz, 1H); 6.23 (dt, Jd=15.9, Jt=6.2 Hz, 1H); 5.92 (d, J=2.2 Hz, 1H); 5.58 (s, 1H); 5.19 & 5.15 (two doublets as ABq, J=12.6 Hz, 2H); 3.73 (dd, J=17.1, 3.0 Hz, 1H); 3.29 (d, J=16.8 Hz, 1H); 3.18 (d, J=5.5 Hz, 2H).

Example 27

(5R)-3-[1-Carboxy-methylidene]-7-oxo-2-(3-phenyl-allyl)-4-oxa-1-aza-bicyclo[3.2.0]heptane-2-carboxylic acid benzyl ester Analogously to the method as described in Examples 24 and 25, but using the compound of Example 6, the title compound is obtained as a powder, having characterization data as indicated below.

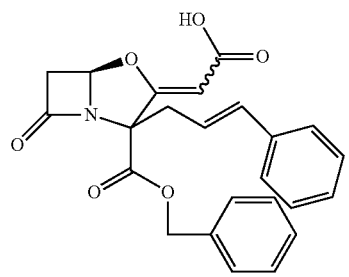

PatAZ9497H $^1$H-NMR (DMSO-d$_6$, 400 MHz): δ 11.96 (br. s, 1H); 7.39-7.23 (m, 10H); 6.55 (d, J=15.9 Hz, 1H); 6.11 (dt, Jd=15.9, Jt=7.4 Hz, 1H); 5.81 (d, J=2.0 Hz, 1H); 5.29 (d, J=12.6 Hz, 1H); 5.13 (d, J=12.4 Hz, 1H); 5.00 (s, 1H); 3.58 (dd, J=17.0, 3.1 Hz, 1H); 3.30 (dd overlapping with H$_2$O-signal, J ca. 17.0, 0.7 Hz, 1H); 2.96 (ddd, J=0.9, 7.4, 14.2 Hz, 1H); 2.82 (ddd, J=0.9, 7.4, 14.4 Hz, 1H).

Example 28

(5R)-3-[1-Carboxy-methylidene]-7-oxo-2-(3-phenyl-allyl)-4-oxa-1-aza-bicyclo[3.2.0]heptane-2-carboxylic acid benzyl ester (isomer of compound of Example 27)

Analogously to the method as described in Examples 24 and 25, but using the compound of Example 5, the title compound is obtained as a gum having characterization data as indicated below.

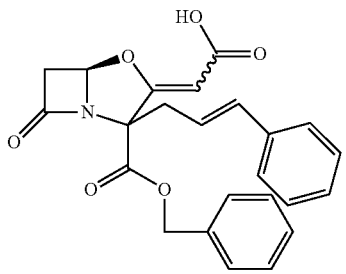

PatAZ9495H ¹H-NMR (DMSO-d₆, 400 MHz): δ 12.07 (br. s, 1H); 7.34-7.23 (m, 10H); 6.56 (d, J=16.1 Hz, 1H); 6.28 (ddd, J=15.9, 8.5, 5.6 Hz, 1H); 5.87 (d, J=2.4 Hz, 1H); 5.22 & 5.18 (two doublets as ABq, J=12.6 Hz, 2H); 5.17 (s, 1H); 3.68 (dd, J=17.0, 3.1 Hz, 1H); 3.32 (d, J=17.0 Hz, 1H); 3.25 (dd, J=8.5, 14.9 Hz, 1H); 2.98 (ddd, J=1.4, 5.6, 14.6 Hz, 1H).

Example 29

Potassium 2-((5R)-2-benzyloxycarbonyl-7-oxo-4-oxa-1-aza-bicyclo[3.2.0]hept-3-ylidene)-5-phenyl-pent-4-enoate A mixture of 109 mg of potassium acetate and 6 ml of i-propanol is added dropwise to a mixture of 468 mg of the compound of Example 26 and 6 ml of i-propanol. The mixture is stirred for 15 minutes and the solvents are removed under vacuum to obtain a residue. The residue is triturated with 5 ml of i-propanol. The precipitate formed is filtered and dried. The title compound is obtained as a powder, having characterization data as indicated below.

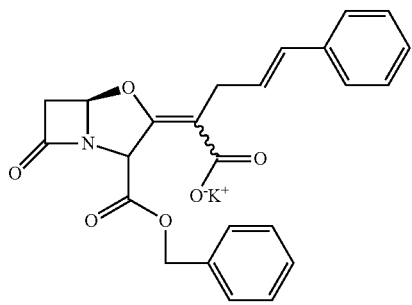

PatAZ8241i ¹H-NMR (DMSO-d₆, 500 MHz): δ 7.39-7.25 (m, 10H); 6.34-6.25 (ABx multiplet, J(AB)=16.0, J(Bx)=5.0 Hz, 2H); 5.65 (s, 1H); 5.61 (d, J=2.3 Hz, 1H); 5.09 (s, 2H); 3.57 (dd, J=17.0, 2.8 Hz, 1H); 3.17 (dd, J=14.2, 4.6 Hz, 1H); 3.10 (dd, J=14.0, 4.8 Hz, 1H); 3.05 (d, J=16.5 Hz, 1H).

Example 30

(5R)-3-(5-Bromo-1-carboxy-pent-3-enylidene)-7-oxo-4-oxa-1-aza-bicyclo[3.2.0]heptane-2-carboxylic acid benzyl ester Analogously to the method as described in Examples 24 and 25, but using the compound of Example 20, the title compound is obtained as an oil, having characterization data as indicated below.

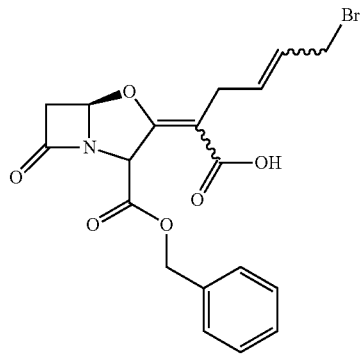

PatAZ7207k ¹H-NMR (DMSO-d₆, 400 MHz): mixture of isomers; data of main isomer: δ 7.43-7.31 (m, 5H); 5.89 (d, J=2.4 Hz, 1H); 5.82 (dt, Jd=15.0, Jt=6.0 Hz, 1H); 5.65 (dt as quintet, Jd=15.2, Jt=7.5 Hz, 1H); 5.54 (s, 1H); 5.16 (s, 2H); 4.07 (d, J=7.3 Hz, 2H); 3.73 (dd, J=2.9, 17.0 Hz, 1H); 3.27 (d, J=17.2 Hz, 1H), 3.02 (d, J=5.7 Hz, 2H).

Example 31

(5R)-3-(5-Azido-1-carboxy-pent-3-enylidene)-7-oxo-4-oxa-1-aza-bicyclo[3.2.0]heptane-2-carboxylic acid benzyl ester Analogously to the method as described in Examples 24 and 25, but using the compound of Example 23, the title compound is obtained as an oil, having characterization data as indicated below.

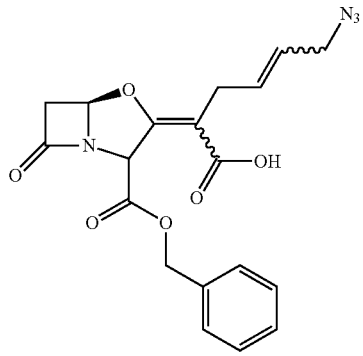

PatAZ7202k ¹H-NMR (DMSO-d₆, 500 MHz): mixture of isomers; data of main isomer: δ 12.7-12.0 (br. s); 7.5-7.3 (m, 5H); 5.88 (d, J=2.6 Hz, 1H); 5.84-5.74 (m, 1H); 5.54 (s, 1H); 5.53-5.46 (m, 1H); 5.15 (s, 2H); 3.26 (d, J=17.2 Hz, 1H); 3.04 (d, J=6.0 Hz, 2H).

Example 32

(5R)-3-(1-Carboxy-but-3-enylidene)-7-oxo-4-oxa-1-aza-bicyclo[3.2.0]heptane-2-carboxylic acid methyl ester Analogously to the method as described in Examples 24 and 25, but using the compound of Example 16, the title compound is obtained as an oil, having characterization data as indicated below.

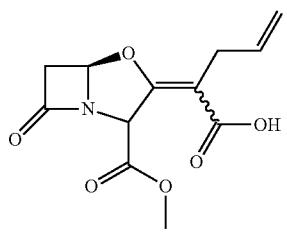

PatAZ8283i ¹H-NMR (DMSO-d₆, 400 MHz): δ 12.43 (br. s, 1H); 5.87 (d, J=2.7 Hz, 1H); 5.81 (ddt, Jd=17.2, 10.1, Jt=5.7 Hz, 1H); 5.49 (s, 1H); 5.01 (dd, J=17.2, 1.8 Hz, 1H); 4.95 (dd, J=10.1, 1.5 Hz, 1H); 3.71 (dd, J=17.1, 3.0 Hz, 1H); 3.67 (s, 3H); 3.25 (d, J=17.0 Hz, 1H); 3.01 (d, J=5.7 Hz, 2H).

Example 33

(5R)-2-Allyl-3-carboxymethylidene-7-oxo-4-oxa-1-aza-bicyclo[3.2.0]heptane-2-carboxylic acid methyl ester Analogously to the method as described in Examples 24 and 25, but using the compound of Example 17, the title compound is obtained as a foam, having characterization data as indicated below.

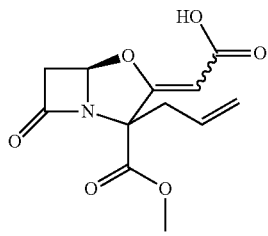

PatAZ8297i ¹H-NMR (DMSO-d₆, 400 MHz): mixture of isomers; δ 12.00 (br. s); 5.84 (d, J=2.7 Hz, 1H, major isomer); 5.79 (d, J=2.2 Hz, 1H, minor isomer); 5.09 (s, 1H, major); 4.95 (s, 1H, minor); 3.71 (s, 3H, minor); 3.70 (s, 3H, major); 3.66 (dd, J=2.9, 17.0 Hz, 1H, major); 3.56 (dd, J=2.9, 17.0 Hz, 1H, minor); 3.33 (d overlapping with H₂O signal); 3.28 (d, J=17.0 Hz, 1H, major); 3.04 (dd, J=8.6, 14.6 Hz, 1H, major); 2.62 (dd, J=7.1, 14.3 Hz, 1H, minor).

Example 34

(5R)-3-(1-Carboxy-4-phenyl-but-3-enylidene)-7-oxo-4-oxa-1-aza-bicyclo[3.2.0]heptane-2-carboxylic acid methyl ester Analogously to the method as described in Examples 24 and 25, but using the compound of Example 13, the title compound is obtained as an oil, having characterization data as indicated below.

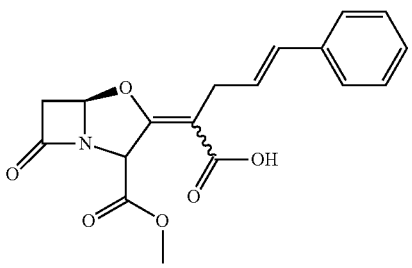

PatAZ8260i ¹H-NMR (DMSO-d₆, 400 MHz): δ 12.54 (br. s, 1H); 7.37-7.14 (m, 5H); 6.39 (d, J=16.1 Hz, 1H); 6.26 (dt, Jd=15.9, Jt=6.0 Hz, 1H); 5.91 (d, J=2.7 Hz, 1H); 5.53 (s, 1H); 3.74 (dd, J=17.2, 3.1 Hz, 1H); 3.69 (s, 3H); 3.29 (d, J=17.2 Hz, 1H); 3.18 (d, J=5.7 Hz, 2H).

Example 35

(5R)-3-[1-Carboxy-methylidene]-7-oxo-2-(3-phenyl-allyl)-4-oxa-1-aza-bicyclo[3.2.0]heptane-2-carboxylic acid methyl ester Analogously to the method as described in Examples 24 and 25, but using the compound of Example 15, the title compound is obtained as a foam, having characterization data as below.

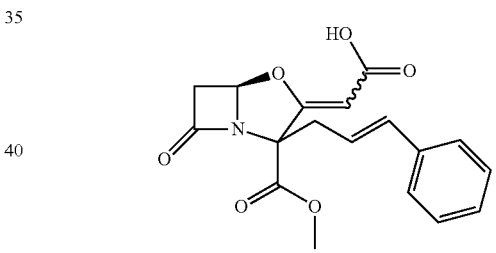

PatAZ8280i ¹H-NMR (DMSO-d₆, 400 MHz): δ 11.97 (br. s, 1H); 7.41-7.23 (m, 5H); 6.56 (d, J=15.9 Hz, 1H); 6.13 (dt, Jd=15.9, Jt=7.3 Hz, 1H); 5.78 (d, J=2.2 Hz, 1H); 5.01 (s, 1H); 3.73 (s, 3H); 3.56 (dd, J=2.9, 17.0 Hz, 1H); 3.33 (d, J=16.3 Hz, 1H); 2.96 (dd, J=7.3, 15.0 Hz, 1H); 2.79 (dd, J=7.3, 15.0 Hz, 1H).

Example 36

(5R)-3-[1-Carboxy-methylidene]-7-oxo-2-(3-phenyl-allyl)-4-oxa-1-aza-bicyclo[3.2.0]heptane-2-carboxylic acid methyl ester (isomer of compound of Example 35)

Analogously to the method as described in Examples 24 and 25, but using the compound of Example 14, the title compound is obtained as a foam, having characterization data as indicated below.

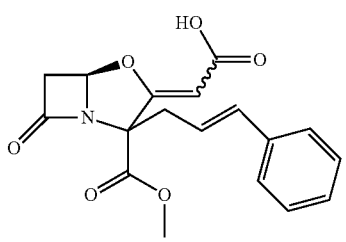

PatAZ8262i $^1$H-NMR (DMSO-$d_6$, 400 MHz): δ 12.05 (br. s, 1H); 7.37-7.23 (m, 5H); 6.62 (d, J=15.9 Hz, 1H); 6.32 (ddd, J=15.9, 8.4, 5.5 Hz, 1H); 5.87 (d, J=2.7 Hz, 1H); 5.15 (s, 1H); 3.71 (s, 3H); 3.68 (dd, J=2.9, 17.0 Hz, 1H); 3.32 (d, J=17.0 Hz, 1H); 3.22 (dd, J=8.6, 14.8 Hz, 1H); 2.97 (ddd, J=1.3, 5.5, 14.6 Hz, 1H).

Example 37

(5R)-3-(1-Carboxy-4-phenyl-but-3-enylidene)-7-oxo-4-oxa-1-aza-bicyclo[3.2.0]heptane-2-carboxylic acid 2,2-dimethyl-propionyloxymethyl ester Analogously to the method as described in Examples 24 and 25, but using the compound of Example 18, the title compound is obtained as a powder, having characterization data as indicated below.

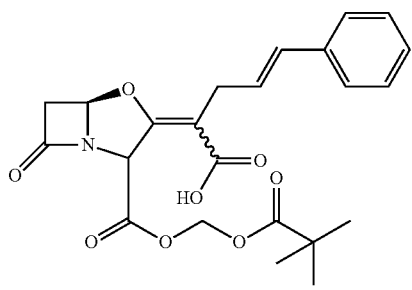

PatAZ9496H $^1$H-NMR (DMSO-$d_6$, 400 MHz): δ 12.50 (br. s, 1H); 7.36 (d, J=7.1 Hz, 2H); 7.29 (t, J=7.6 Hz, 2H); 7.19 (tt, J=7.3, 1.6 Hz, 1H); 6.38 (d, J=15.9 Hz, 1H); 6.24 (dt, Jd=15.9, Jt=6.0 Hz, 1H); 5.88 (d, J=2.4 Hz, 1H); 5.79 & 5.73 (two doublets as ABq, J=5.8 Hz, 2H); 5.54 (s, 1H); 3.75 (dd, J=17.2, 3.1 Hz, 1H); 3.31 (d overlapping with other signals, J ca. 17.0 Hz, 1H); 3.17 (d, J=5.7 Hz, 2H); 1.11 (br. s, 9H).

Example 38, 38a

Example 38

(5R)-3-[1-Hydroxymethyl-but-3-en-(E)-ylidene]-7-oxo-4-oxa-1-aza-bicyclo[3.2.0]heptane-2-carboxylic acid benzyl ester Example 38a (5R)-3-[1-Hydroxymethyl-but-3-en-(Z)-ylidene]-7-oxo-4-oxa-1-aza-bicyclo[3.2.0]heptane-2-carboxylic acid benzyl ester

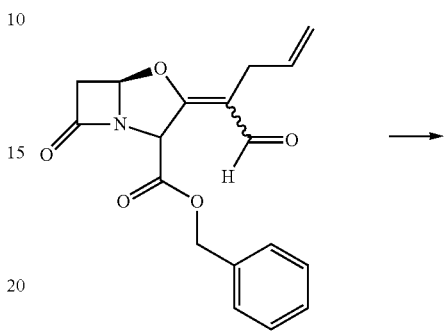

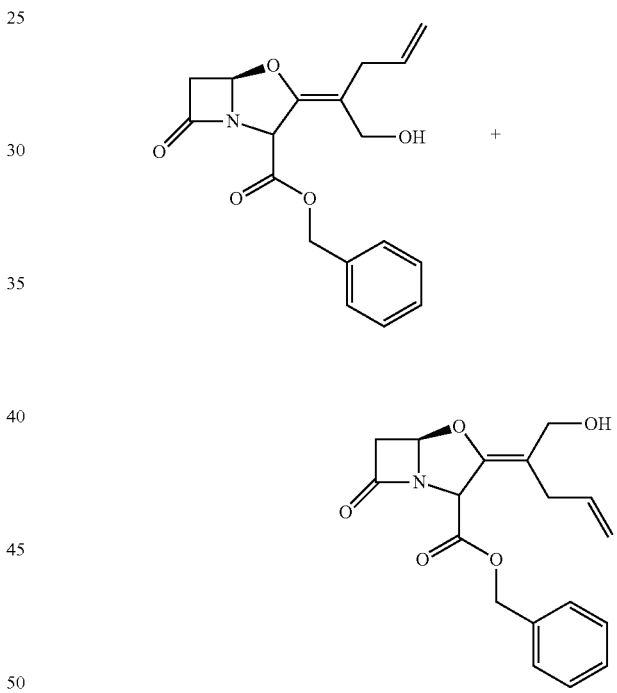

To an ice cold mixture of the compound of Example 1 (7.5 g), 300 ml of tetrahydrofuran and 100 ml of phosphate buffer (pH 7) is added a solution of NaBH$_4$ (693 mg) in 100 ml of water in 4 equal portions in time intervals of 10 minutes under stirring. After a total reaction time of 40 min the mixture is partitioned between 1200 ml of ethyl acetate and 2.4 liter of water and 960 ml brine. The aqueous phase is extracted twice with 600 ml of ethyl acetate each. The organic extracts are combined, dried (MgSO$_4$) and stripped of the solvents to give an oil which is subjected to chromatography over an SiO$_2$ column using toluene/t-butyl methyl ether=7/1. The compound of Example 38 as an oil, having characterization data as indicated below

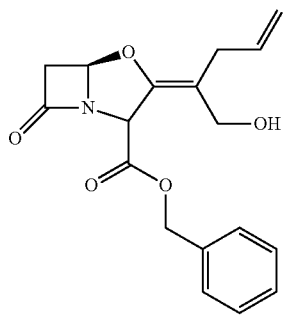

PatAZ9457h ¹H-NMR (DMSO-d₆, 400 MHz): δ 7.46-7.32 (m, 5H); 5.78-5.70 (m, 1H); 5.67 (d, J=2.7 Hz, 1H); 5.46 (s, 1H); 5.17 (s, 2H); 4.97 (dd, J=15.0, 1.8 Hz, 1H); 4.93 (dd, J=7.7, 1.8 Hz, 1H); 4.68 (dd, J=5.0, 6.1 Hz, 1H); 3.93 (dd, J=4.7, 12.9 Hz, 1H); 3.72 (dd, J=6.2, 13.0 Hz, 1H); 3.61 (dd, J=17.0, 2.9 Hz, 1H); 3.05 (d, J=16.8 Hz, 1H); 2.87 (dd, J=14.8, 6.0 Hz, 1H); 2.80 (dd, J=14.8, 6.7 Hz, 1H),
and the compound of Example 38a as an oil, having characterization data as indicated below

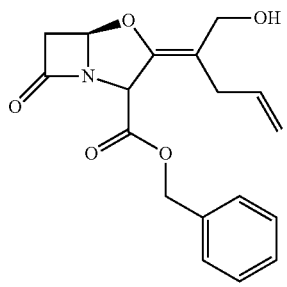

PatAZ7225k ¹H-NMR (DMSO-d₆, 500 MHz): δ 7.40-7.35 (m, 5H); 5.70 (d, J=2.7 Hz, 1H); 5.63-5.53 (m, 1H); 5.33 (s, 1H); 5.18 and 5.14 (2 d as ABq, J=12.5 Hz, 2H); 4.91 (d, J=18.1 Hz, 1H); 4.91 (d, J=9.9 Hz, 1H); 4.60 (dd, J=5.5, 4.9 Hz, 1H); 4.10 (dd, J=4.9, 12.1 Hz, 1H); 3.86 (dd, J=6.0, 12.1 Hz, 1H); 3.62 (dd, J=17.0, 2.9 Hz, 1H); 3.09 (d, J=17.0 Hz, 1H); 2.80 (dd, J=15.5, 7.1 Hz, 1H); 2.73 (dd, J=15.4, 5.5 Hz, 1H);
are obtained.

Example 39

(5R)-3-(1-Hydroxymethyl-4-phenyl-but-3-enylidene)-7-oxo-4-oxa-1-aza-bicyclo[3.2.0]heptane-2-carboxylic acid benzyl ester Analogously to the method as described in Example 38 and 38a, but using the compound of Example 4, the title compound is obtained as an oil, having characterization data as indicated below.

PatAZ8220i ¹H-NMR (DMSO-d₆, 400 MHz): δ 7.36-7.27 (m, 10H); 6.37 (d, J=15.9 Hz, 1H); 6.20 (dt, Jd=15.9, Jt=6.6 Hz, 1H); 5.71 (d, J=2.4 Hz, 1H); 5.50 (s, 1H); 5.17 (s, 2H); 4.73 (dd, J=6.2, 4.9 Hz, 1H); 3.97 (dd, J=13.0, 4.9 Hz, 1H); 3.78 (dd, J=13.0, 6.2 Hz, 1H); 3.63 (dd, J=2.9, 17.0 Hz, 1H); 3.08 (dd, J=17.0, 0.5 Hz, 1H); 3.03-2.96 (m, 2H).

Example 40

(5R)-2-Allyl-3-[2-hydroxy-ethylidene]-7-oxo-4-oxa-1-aza-bicyclo[3.2.0]heptane-2-carboxylic acid benzyl ester Analogously to the method as described in Examples 38 and 38a, but using the compound of Example 2, the title compound is obtained as an oil, having characterization data as indicated below.

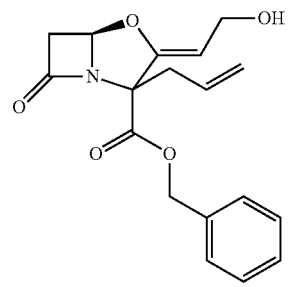

PatAZ2522i ¹H-NMR (DMSO-d₆, 400 MHz): mixture of isomers: δ 7.43-7.31 (m); 5.97-5.86 (m, 1H); 5.79-5.69 (m, 0.5H); 5.58 (d, J=2.7 Hz, 1H); 5.47 (d, J=2.4 Hz, 0.5H); 5.23 (d, J=12.8 Hz, 0.5H); 5.20-5.10 (overlapping multiplets, 5H); 5.05 (d, J=12.6 Hz, 0.5H); 4.78 (t, J=6.7 Hz, 1H); 4.65 (t, J=5.6 Hz); 4.61 (t, J=6.9 Hz); 4.09-3.93 (overlapping multiplets, 3H); 3.55 (dd, J=2.9, 16.8 Hz, 1H); 3.41 (dd, J=2.9, 16.8 Hz, 0.5H); 3.10 (d, J=16.5 Hz, 0.5H); 3.09 (d, J=16.8 Hz, 1H); 3.00 (dd, J=8.6, 14.6 Hz, 1H); 2.77-2.71 (overlapping multiplets, 1.5H); 2.54-2.50 (m overlapping with DMSO).

Examples 41 and 42

Example 41

(5R)-3-(5-Iodomethyl-2-oxo-dihydro-furan-3-ylidene)-7-oxo-4-oxa-1-aza-bicyclo[3.2.0]heptane-2-carboxylic acid benzyl ester

Example 42

(5R)-3-(5-Iodomethyl-2-oxo-dihydro-furan-3-ylidene)-7-oxo-4-oxa-1-aza-bicyclo[3.2.0]heptane-2-carboxylic acid benzyl ester (isomer of compound of Example 41)

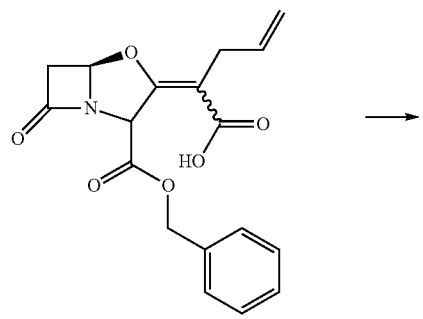

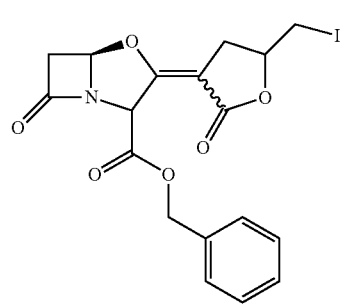

A mixture of the compound of Example 24 (1.63 g), 83 ml of tetrahydrofuran, pyridine (0.765 ml) and iodine (2.41 g) is stirred at room temperature. At time points of 50 minutes and 2 hours 40 minutes further amounts of pyridine (0.115 ml) and iodine (0.362 g) are added. After a total reaction time of 3 hours 40 minutes the solvents are removed under vacuum and the residue is taken up in 330 ml of ethyl acetate and washed with aqueous 5% sodium thiosulfate.5H$_2$O, cold aqueous 0.1% NaHSO$_4$, cold aqueous 0.5% NaHCO$_3$ and then brine. The organic extract is dried (MgSO$_4$) and stripped of the solvents to obtain a gum which is subjected to chromatography twice over a SiO$_2$ column using toluene/t-butyl methyl ether (92/8). The compound of Example 41 as a gum, having characterization data as indicated below

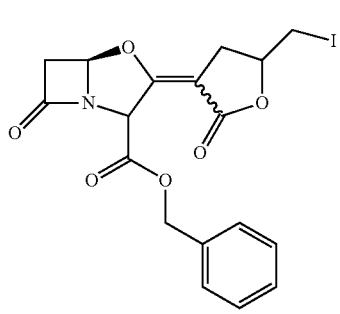

retention factor (SiO2-tlc plate, toluene/t-butyl methyl ether=3/1)=0.65;
PatAZ1889k less polar isomer $^1$H-NMR (DMSO-d$_6$, 500 MHz): δ 7.41-7.33 (m, 5H); 5.99 (d, J=2.7 Hz, 1H); 5.55 (s, 1H); 5.21 & 5.17 (two doublets as ABq, J=12.7 Hz, 2H); 4.65 (m, 1H); 3.77 (dd, J=3.0, 17.0 Hz, 1H); 3.53 & 3.49 (two overlapping multiplets, 2H); 3.36 (d, J=17.4 Hz, 1H); 3.10 (ddd, J=1.3, 8.7, 16.7 Hz, 1H); 2.60 (ddd, J=1.3, 5.4, 16.7 Hz, 1H);
and the compound of Example 42 as a gum, having characterization data as indicated below retention factor (SiO2-tlc plate, toluene/t-butyl methyl ether=3/1)=0.56; PatAZ1890k more polar isomer $^1$H-NMR (DMSO-d$_6$, 500 MHz): δ 7.40-7.33 (m, 5H); 6.01 (d, J=2.7 Hz, 1H); 5.55 (s, 1H); 5.19 & 5.16 (two doublets as very close ABq, J=12.7 Hz, 2H); 4.59 (m, 1H); 3.77 (dd, J=3.4, 17.4 Hz, 1H); 3.52 (dd, J=4.7, 10.7 Hz, 1H); 3.46 (dd, J=4.7, 10.7 Hz, 1H); 3.34 (d, J=17.4 Hz, 1H); 3.08 (ddd, J=1.3, 8.0, 16.7 Hz, 1H); 2.56 (ddd, J=1.3, 5.4, 16.7 Hz, 1H);
are obtained.

Examples 43 and 44

Example 43

(5R)-3-(5-Iodomethyl-2-oxo-dihydro-furan-3-ylidene)-7-oxo-4-oxa-1-aza-bicyclo[3.2.0]heptane-2-carboxylic acid methyl ester

Example 44

(5R)-3-(5-Iodomethyl-2-oxo-dihydro-furan-3-ylidene)-7-oxo-4-oxa-1-aza-bicyclo[3.2.0]heptane-2-carboxylic acid methyl ester (isomer of compound of Example 43)

Analogously to the method as described in Examples 41 and 42, but using the compound of Example 32, the compound of Example 43 as a foam, having characterization data as indicated below

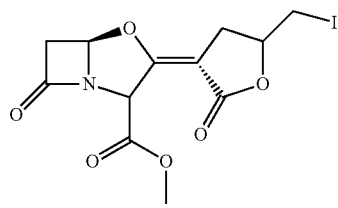

Elution order over SiO2-chromatography using toluene/t-butyl methyl ether: the compound of Example 43 is eluted before the compound of Example 44.

PatAZ1822k less polar isomer $^1$H-NMR (DMSO-d$_6$, 400 MHz): δ 6.00 (d, J=2.9 Hz, 1H); 5.49 (s, 1H); 4.59 (m, 1H); 3.76 (dd, J=17.2, 2.9 Hz, 1H); 3.69 (s, 3H); 3.56 (dd, J=10.8, 4.9 Hz, 1H); 3.52 (dd, J=10.8, 4.6 Hz, 1H); 3.33 (d overlapping with H$_2$O-signal, 1H); 3.08 (ddd, J=1.1, 8.3, 16.6 Hz, 1H); 2.57 (ddd, J=1.5, 5.5, 16.8 Hz, 1H);

and the compound of Example 44 as a foam, having characterization data as indicated below

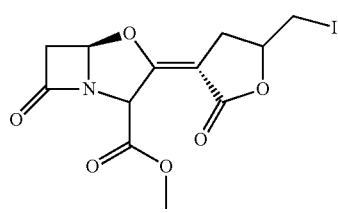

Elution order over SiO2-chromatography using toluene/t-butyl methyl ether: the compound of Example 44 is eluted after compound of Example 43.

Pat AZ1823k more polar isomer $^1$H-NMR (DMSO-d$_6$, 400 MHz): δ 5.99 (d, J=2.7 Hz, 1H); 5.49 (s, 1H); 4.66 (m, 1H); 3.77 (dd, J=17.2, 3.1 Hz, 1H); 3.69 (s, 3H); 3.52 (dd, J=14.6, 5.0 Hz, 1H); 3.49 (dd, J=14.6, 5.0 Hz, 1H); 3.35 (d, J=17.2 Hz, 1H); 3.11 (ddd, J=1.6, 8.5, 16.8 Hz, 1H); 2.59 (ddd, J=1.5, 5.1, 16.8 Hz, 1H);

are obtained.

Example 45

(5R)-3-(5-Methyl-2-oxo-dihydro-furan-3-ylidene)-7-oxo-4-oxa-1-aza-bicyclo[3.2.0]heptane-2-carboxylic acid benzyl ester

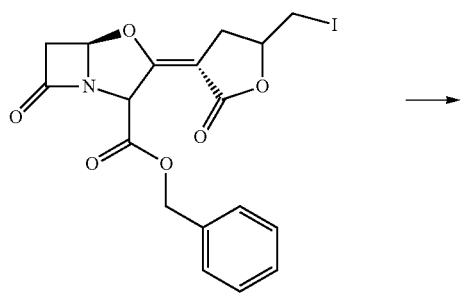

→

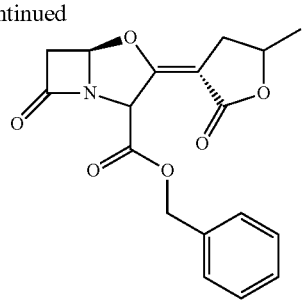

A mixture of 1800 mg of 10% Pd/C and 390 ml of ethyl acetate is stirred at room temperature under hydrogen atmosphere for 30 minutes. A solution of the compound of Example 41 (800 mg) in 10 ml of ethyl acetate is introduced with a syringe, and stirring is continued under hydrogen atmosphere. At time points of 1 hour 20 minutes, 2 hour 40 minutes, 4 hour and 5 hour 35 minutes further amounts of 1800 mg 10% Pd/C each are added. After a total reaction time of 6 hours 50 minutes, the mixture is filtered through celite and stripped of the solvents to obtain a residue which is subjected to chromatography thrice over SiO$_2$ using toluene/t-butyl methyl ether (17/1). The title compound is obtained as a foam, having characterization data as indicated below.

PatAZ1815k less polar I series $^1$H-NMR (DMSO-d$_6$, 400 MHz): δ 7.40-7.34 (m, 5H); 5.96 (d, J=2.7 Hz, 1H); 5.57 (t, J=1.6 Hz, 1H); 5.18 (ABq as pseudo t, J=13.3 Hz, 2H); 4.76-4.67 (m, 1H); 3.76 (dd, J=3.0, 17.0 Hz, 1H); 3.33 (d overlapping with H$_2$O signal, 1H); 3.10 (ddd, J=1.7, 8.0, 16.3 Hz, 1H); 2.50 (ddd buried under DMSO, J=1.8, 5.7, 16.5 Hz, 1H); 1.32 (d, J=6.2 Hz, 3H).

Example 46

(5R)-3-(5-Methyl-2-oxo-dihydro-furan-3-ylidene)-7-oxo-4-oxa-1-aza-bicyclo[3.2.0]heptane-2-carboxylic acid benzyl ester (isomer of compound of Example 45)

Analogously to the method as described in Example 45, but using the compound of Example 42, the title compound is obtained as an oil, having characterization data as indicated below.

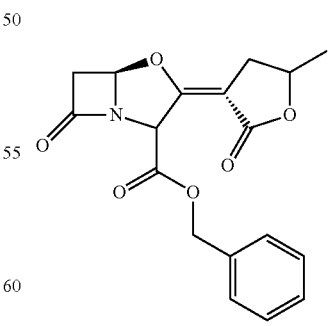

PatAZ1813k more polar iodide series $^1$H-NMR (DMSO-d$_6$, 400 MHz): δ 7.40-7.33 (m, 5H); 5.97 (d, J=2.7 Hz, 1H); 5.56 (t, J=1.1 Hz, 1H); 5.20 & 5.16 (two doublets as ABq, J=12.8 Hz, 2H); 4.75-4.67 (m, 1H); 3.76 (dd, J=3.0, 17.0 Hz, 1H); 3.33 (overlapping d, 1H); 3.09 (ddd, J=1.5, 7.9, 16.3 Hz, 1H); 2.48 (m buried under DMSO); 1.29 (d, J=6.2 Hz, 3H).

Example 47

(5R)-3-(5-Azidomethyl-2-oxo-dihydro-furan-3-ylidene)-7-oxo-4-oxa-1-aza-bicyclo[3.2.0]heptane-2-carboxylic acid benzyl ester

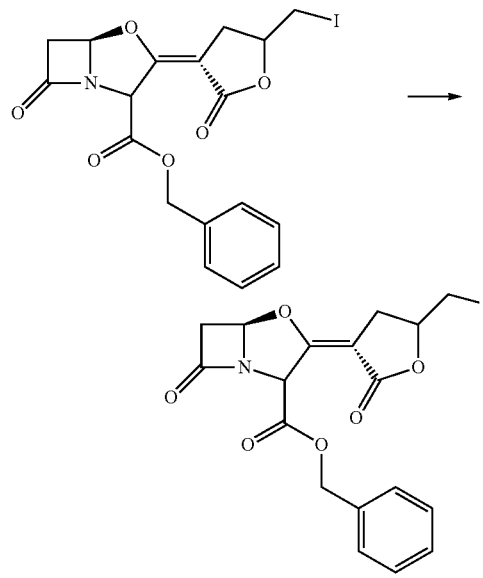

A mixture of the compound of Example 41 (500 mg), 50 ml of tetrahydrofuran and tetrabutylammonium azide (364 mg) is stirred at room temperature for 30 minutes. The mixture is partitioned between ethyl acetate and brine. The organic phase is separated, washed with brine, dried (MgSO$_4$) and stripped of the solvents. The residue is subjected to chromatography over an SiO$_2$ column using toluene/t-butyl methyl ether (12/1). The title compound is obtained as an oil, having characterization data as indicated below.

PatAZ1876k less polar I series $^1$H-NMR (DMSO-d$_6$, 400 MHz): δ 7.45-7.31 (m, 5H); 5.99 (d, J=2.7 Hz, 1H); 5.58 (t, J=1.1 Hz, 1H); 5.21 & 5.16 (two doublets as ABq, J=12.7 Hz, 2H); 4.84-4.78 (symmetrical 9-line m, 1H); 3.77 (dd, J=3.0, 17.1 Hz, 1H); 3.64 (dd, J=3.4, 13.3 Hz, 1H); 3.56 (dd, J=6.0, 13.5 Hz, 1H); 3.35 (d overlapping with H$_2$O signal); 3.06 (ddd, J=1.5, 8.6, 16.8 Hz, 1H); 2.64 (ddd, J=1.5, 5.3, 16.8 Hz, 1H).

Example 48

(5R)-3-(5-Azidomethyl-2-oxo-dihydro-furan-3-ylidene)-7-oxo-4-oxa-1-aza-bicyclo[3.2.0]heptane-2-carboxylic acid benzyl ester (isomer of compound of Example 47)

Analogously to the method as described in Example 47, but using the compound of Example 42, the title compound is obtained as a foam, having characterization data as indicated below.

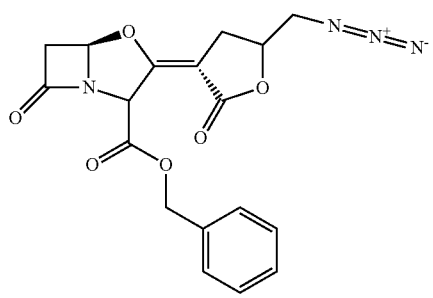

PatAZ1839k more polar I series $^1$H-NMR (DMSO-d$_6$, 400 MHz): δ 7.46-7.30 (m, 5H); 6.00 (d, J=2.4 Hz, 1H); 5.57 (t, J=1.7 Hz, 1H); 5.18 (s, 2H); 4.83-4.78 (symmetrical 9-line m, 1H); 3.77 (dd, J=3.1, 17.2 Hz, 1H); 3.67 (dd, J=3.1, 13.5 Hz, 1H); 3.49 (dd, J=5.6, 13.6 Hz, 1H); 3.34 (d, J=17.0 Hz, 1H); 3.03 (ddd, J=1.5, 8.6, 16.5 Hz, 1H); 2.65 (ddd, J=1.7, 5.5, 16.8 Hz, 1H).

Example 49

(5R)-3-(5-Methyl-2-oxo-dihydro-furan-3-ylidene)-7-oxo-4-oxa-1-aza-bicyclo[3.2.0]heptane-2-carboxylic acid

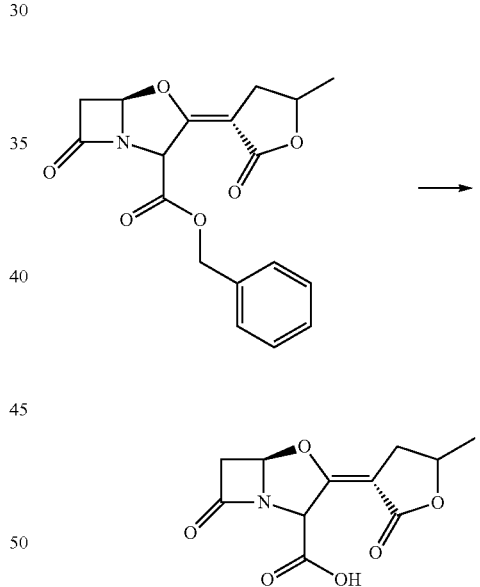

A mixture of 750 mg of 10% Pd/C and 140 ml of ethyl acetate is stirred at 0-5° C. under hydrogen atmosphere for 30 minutes. A solution of the compound of Example 45 (448 mg) in 10 ml of ethyl acetate is introduced with a syringe and stirring is continued for 1 hour 15 minutes under hydrogen atmosphere at 0-5° C. The mixture is filtered through celite and stripped of the solvent. The title compound is obtained as a foam, having characterization data as indicated below.

PatAZ1818k less polar I-series $^1$H-NMR (DMSO-d$_6$, 400 MHz): δ 5.92 (d, J=2.7 Hz, 1H); 5.41 (s, 1H); 4.74-4.66 (m, 1H); 3.72 (dd, J=2.9, 17.0 Hz, 1H); 3.27 (d overlapping with H$_2$O); 3.08 (ddd, J=1.3, 8.2, 16.3 Hz, 1H); 2.48 (m partly buried under DMSO); 1.31 (d, J=6.4 Hz, 3H).

Example 50

(5R)-3-(5-Methyl-2-oxo-dihydro-furan-3-ylidene)-7-oxo-4-oxa-1-aza-bicyclo[3.2.0]heptane-2-carboxylic acid (isomer of compound of Example 49)

Analogously to the method as described in Example 49, but using the compound of Example 46, the title compound is obtained as a foam, having characterization data as indicated below.

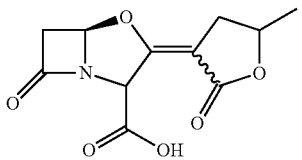

PatAZ1814k more polar I-series $^1$H-NMR (DMSO-$d_6$, 400 MHz): δ 5.94 (d, J=2.7 Hz, 1H); 5.40 (s, 1H); 4.73-4.66 (m, 1H); 3.74 (dd, J=3.0, 17.1 Hz, 1H); 3.27 (d overlapping with $H_2O$); 3.07 (ddd, J=1.2, 7.8, 16.1 Hz, 1H); 2.49 (m buried under DMSO); 1.32 (d, J=6.2 Hz, 3H).

Example 51

(5R)-3-(1-Carboxy-butylidene)-7-oxo-4-oxa-1-aza-bicyclo[3.2.0]heptane-2-carboxylic acid Analogously to the method as described in Example 49, but using the compound of Example 24, the title compound is obtained as a foam, having characterization data as indicated below.

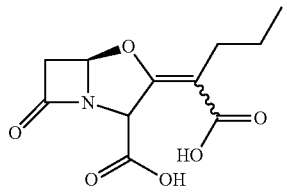

PatAZ8285i $^1$H-NMR (DMSO-$d_6$, 400 MHz): δ 13.5-12.2 (br. s, 1H); 5.81 (d, J=2.7 Hz, 1H); 5.38 (s, 1H); 3.69 (dd, J=2.9, 17.0 Hz, 1H); 3.19 (d, J=17.0 Hz, 1H); 2.23 (t, J=7.5 Hz, 2H); 1.45-1.35 (m, 2H); 0.85 (t, J=7.4 Hz, 3H).

Example 52

(5R)-3-(1-Carboxy-4-phenyl-butylidene)-7-oxo-4-oxa-1-aza-bicyclo[3.2.0]heptane-2-carboxylate-1,1,3,3-tetramethyl-butyl-ammonium Analogously to the method as described in Example 49, but using the compound of Example 26, (5R)-3-(1-carboxy-4-phenyl-butylidene)-7-oxo-4-oxa-1-aza-bicyclo[3.2.0]heptane-2-carboxylic acid is obtained as a foam. A mixture of the foam, ethyl acetate and 1,1,3,3-tetramethyl-butyl-amine is stirred at 0-5° C. After 30 minutes, the solvent is removed under vacuum and the residue is dissolved in 1 ml of dichloromethane, 3 ml of petroleum ether are added to it in small portions and the mixture is allowed to stand for 15 minutes. The precipitate formed is filtered, washed with petroleum ether and dried. The title compound is obtained as a powder, having characterization data as indicated below.

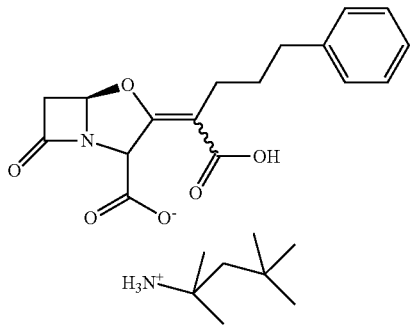

PatAZ8230i $^1$H-NMR (DMSO-$d_6$, 400 MHz): δ 7.27-7.12 (m, 5H); 5.67 (d, J=2.4 Hz, 1H); 5.19 (s, 1H); 3.61 (dd, J=17.0, 2.8 Hz, 1H); 2.99 (d, J=17.0 Hz, 1H); 1.61 (m, 2H); 1.44 (s, 2H); 1.17 (s, 6H); 0.98 (s, 9H).

Example 53

(5R)-3-(1-Carboxy-4-phenyl-butylidene)-7-oxo-4-oxa-1-aza-bicyclo[3.2.0]heptane-2-carboxylic acid methyl ester Analogously to the method as described in Example 49, but using the compound of Example 34, the title compound is obtained as an oil, having characterization data as indicated below.

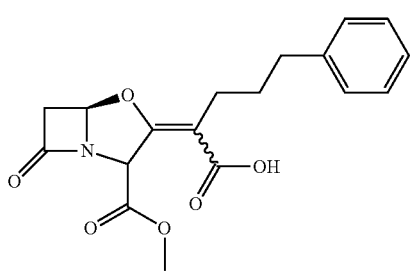

Pat AZ8207i $^1$H-NMR: (DMSO-$d_6$, 400 MHz): δ 12.42 (br. s, 1H); 7.28-7.25 (m, 2H); 7.19-7.14 (m, 3H); 5.85 (d, J=2.8 Hz, 1H); 5.45 (s, 1H); 3.69 (dd, J=3.0, 17.2 Hz, 1H); 3.66 (s, 3H); 3.26 (d, J=17.0 Hz, 1H); 2.61-2.53 (m, 2H); 2.32 (t, J=7.3 Hz, 2H); 1.75-1.65 (m, 2H).

Example 54

(5R)-3-(1-Carboxy-butylidene)-7-oxo-4-oxa-1-aza-bicyclo[3.2.0]heptane-2-carboxylic acid methyl ester Analogously to the method as described in Example 49, but using the compound of Example 32, the title compound is obtained as an oil, having characterization data as indicated below.

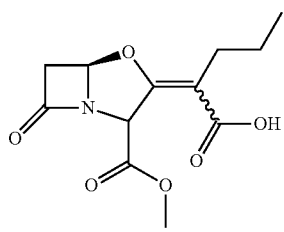

PatAZ8300i ¹H-NMR (DMSO-d₆, 400 MHz): δ 12.49 (br. s); 5.84 (d, J=2.4 Hz, 1H); 5.45 (s, 1H); 3.70 (dd, J=3.0, 17.1 Hz, 1H); 3.66 (s, 3H); 3.25 (d, J=17.2 Hz, 1H); 2.25 (t, J=7.4 Hz, 2H); 1.48-1.37 (m, 2H); 0.86 (t, J=7.4 Hz, 3H).

Example 55

(5R)-3-(1-Hydroxymethyl-butylidene)-7-oxo-4-oxa-1-aza-bicyclo[3.2.0]heptane-2-carboxylate 1,1,3,3-tetramethyl-butyl-ammonium Analogously to the method as described in Example 49, but using the compound of Example 38, (5R)-3-(1-Hydroxymethyl-butylidene)-7-oxo-4-oxa-1-aza-bicyclo[3.2.0]heptane-2-carboxylic acid is obtained as an oil. A mixture of the oil, ethyl acetate and 1,1,3,3-tetramethyl-butyl-amine is stirred at room temperature for 10 minutes. The solvents are removed under vacuum. The title compound is obtained as an oil, having characterization data as indicated below.

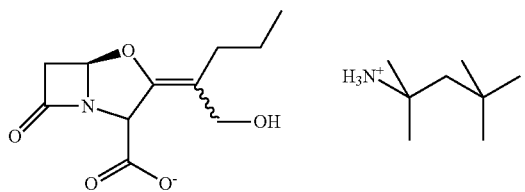

PatAZ2537i ¹H-NMR (DMSO-d₆, 400 MHz): mixture of isomers; data of major isomer: δ 5.48 (d, J=2.7 Hz, 1H); 4.89 (s, 1H); 3.94 & 3.81 (two doublets as ABq, J=13.0 Hz, 2H); 3.44 (dd, J=2.7, 16.3 Hz, 1H); 2.77 (d, J=16.5 Hz, 1H); 2.05-1.93 (m, 2H); 1.39-1.33 (overlapping multiplets); 0.82 (t, J=7.4 Hz, 3H); 1.35 (s, 2H); 1.29 (s, 6H); 0.98 (s, 9H).

Example 56

(5R)-3-[2-Hydroxy-ethylidene]-7-oxo-2-propyl-4-oxa-1-aza-bicyclo[3.2.0]heptane-2-carboxylate 1,1,3,3-tetramethyl-butyl-ammonium Analogously to the method as described in Example 49, but using the compound of Example 40, (5R)-3-[2-Hydroxy-ethylidene]-7-oxo-2-propyl-4-oxa-1-aza-bicyclo[3.2.0]heptane-2-carboxylic acid is obtained as an oil. A mixture of the oil, ethyl acetate and 1,1,3,3-tetramethyl-butyl-amine is stirred at room temperature. The precipitate formed is filtered and dried. The title compound is obtained as a powder, having characterization data as indicated below.

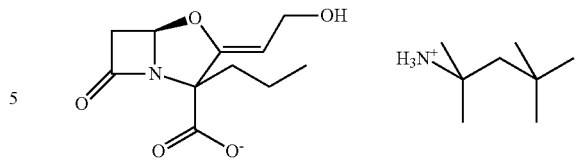

PatAZ2536i ¹H-NMR (D₂O, 400 MHz): mixture of isomers; major isomer: δ 5.59 (d, J=2.4 Hz, 1H); 4.87 (t, J=7.4 Hz, 1H); 4.23 (dd, J=7.8, 12.2 Hz, 1H); 4.16 (dd, J=7.1, 12.1 Hz, 1H); 3.47 (dd, J=2.9, 16.8 Hz, 1H); 3.07 (d, J=16.8 Hz, 1H); 2.16 (ddd, J=13.8, 12.2, 4.5 Hz, 1H); 1.90 (ddd, J=14.1, 12.2, 4.0 Hz, 1H); 1.78-1.67 (overlapping multiplets); 1.43-1.30 (overlapping multiplets); 0.97 (t, J=7.3 Hz, 3H); 1.70 (s, 2H); 1.47 (s, 6H); 1.06 (s, 9H).

Example 57

(5R)-3-(1-Methoxycarbonyl-4-phenyl-butylidene)-7-oxo-4-oxa-1-aza-bicyclo[3.2.0]heptane-2-carboxylic acid methyl ester

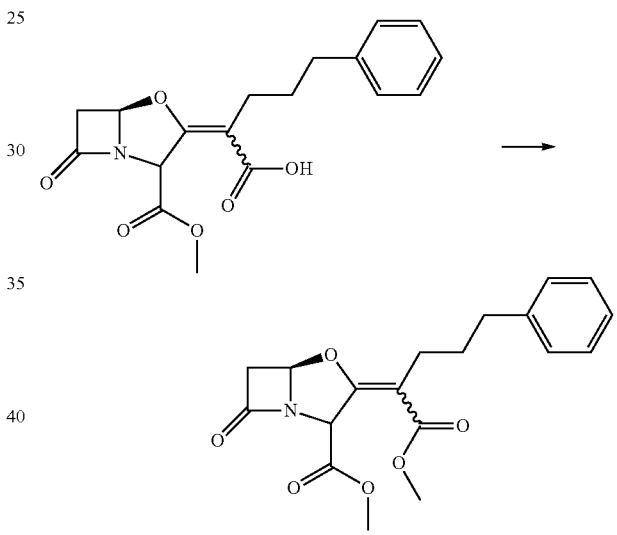

A mixture of the compound of Example 53 (22 mg), 1 ml of ethyl acetate and 0.2 ml of an ethereal solution of diazomethane is stirred at 0-5° C. for 25 minutes. The solvents are removed under vacuum to obtain a residue. The residue is subjected to chromatography over a short SiO₂ column. The title compound is obtained as an oil, having characterization data as indicated below.

PatAZ8208i ¹H-NMR (DMSO-d₆, 400 MHz): 7.28-7.25 (m, 2H); 7.19-7.16 (m, 3H); 5.89 (d, J=2.4 Hz, 1H); 5.47 (s, 1H); 3.71 (dd, J=3.1, 17.0 Hz, 1H); 3.69 (s, 3H); 3.61 (s, 3H); 3.28 (d, J=17.0 Hz, 1H); 2.61-2.52 (m, 2H); 2.34 (t, J=7.5 Hz, 2H); 1.77-1.64 (m, 2H).

Example 58

(5R)-3-[5-(Benzyl-benzyloxycarbonyl-amino)-1-carboxy-pent-3-enylidene]-7-oxo-4-oxa-1-aza-bicyclo[3.2.0]heptane-2-carboxylic acid benzyl ester Analogously to the method described in Examples 24 and 25, but using compound of Example 21, the title compound is obtained as oil, having characterization data as below.

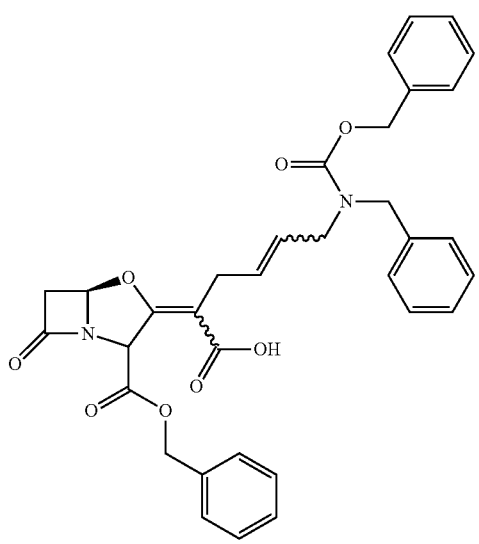

PatAZ 7229k $^1$H-NMR (DMSO-$d_6$, 400 MHz): δ 12.53 (br s, 1H); 7.39-7.16 (m, 15H); 5.85 (d, J=2.7 Hz, 1H); 5.55 (s, 1H); 5.55-5.45 (br, 1H); 5.42-5.35 (m, 1H); 5.14 (s, 2H); 5.09 (s, 2H); 4.34 (s, 2H); 3.72 (dd, J=2.9, 17.0 Hz, 1H); 3.75-3.70 (br, 2H); 3.21 (d, J=17.0 Hz, 1H); 2.98 (d, J=5.5 Hz, 2H).

Example 59

(5R)-3-[5-Iodomethyl-dihydro-furan-3-ylidene]-7-oxo-4-oxa-1-aza-bicyclo[3.2.0]heptane-2-carboxylic acid benzyl ester Analogously to the method as described in Examples 41 and 42, but using the compound of Example 38, the title compound is obtained as an oil, having characterization data as indicated below

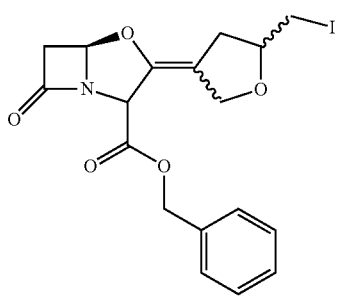

PatAZ7228k $^1$H-NMR (DMSO-$d_6$, 500 MHz): mixture of two isomers; δ 7.41-7.34 (m, 4.5H); 5.73 (2 overlapping doublets, J=2.8, 3.2 Hz, 0.9H); 5.45 (s, 0.3H); 5.39 (s, 0.6H); 5.21 & 5.17 (2 doublets as ABq, J=12.4 Hz, 1.2H); 5.18 (s, 0.6H); 4.48 (d, J=12.4 Hz, 0.3H); 4.33 (d, J=12.4 Hz, 0.6H); 4.19 (d, J=12.4 Hz, 0.6H); 4.01-3.96 (overlapping multiplets, 0.9H); 3.89-3.84 (quintet, J ca. 6 Hz, 0.3H); 3.62 (dd, J=3.2, 17.0 Hz, 0.9H); 3.38 (dd, J=5.3, 10.3 Hz, 0.3H); 3.30 (m); 3.25 (dd, J=10.2, 5.8 Hz, 0.6H); 3.11 (d, J=17.0 Hz, 0.6H); 3.10 (d, J=17.0 Hz, 0.3H); 2.75 (dd, J=6.8, 16.1 Hz, 0.6H); 2.64 (ddd, J=1.4, 6.8, 16.2 Hz, 0.3H); 2.28-2.21 (2 overlapping dd, J ca 7.3, 16.1 Hz, 0.9H).

The inhibitory activity of the compounds of the present invention on β-lactamases is shown by the following examples:

Cell-Free-β-Lactamase Inhibition Study

The inhibitory concentrations (IC50, [μM]) of the β-lactamase inhibitors against purified TEM-1, SHV-1 and AmpC β-lactamases are assessed by determining the concentration of inhibitor at which 50% of the nitrocefin hydrolysis is inhibited by the particular enzyme. Assays are performed with β-lactamases expressed in the pET system (Novagen, San Diego, Calif.) without signal peptides. They contain an N-terminal hexa-Histidine tag that is used for purification on Ni-NTA (Qiagen, Hilden, Germany). The compounds are prepared as 50 mM stocks in DMSO and diluted into buffer P1 (50 mM phosphate, pH 7) to a final concentration of 10% DMSO. All further dilutions are done in P2 (P1 with 10% DMSO). Enzyme and compound dilutions are pre-incubated for 10 min at 37° C. and the reaction is started with the addition of pre-warmed (37° C.) nitrocefin at a final concentration of 50 mM. The change in absorption at 490 nm is followed at 37° C. for 10 min with 30 s intervals in a SPECTRAMAX 384 PLUS microplate reader (Molecular Devices, Sunnyvale, Calif.) using 96 well plates. The initial velocity is determined and IC50 values are calculated using non-linear regression and sigmoidal dose response analysis with the PRISM 4.0 software (Graphpad Software Inc., San Diego, Calif.). $IC_{50}$ data are expressed as μM with 95% confidence interval and are calculated from at least two independent experiments.

$IC_{50}$ Values of the Compounds of the Present Invention and Commercially Available Compounds on β-Lactamase Enzymes:

| Compound | Enzyme | $IC_{50}$ [μM] |
| --- | --- | --- |
| Clavulanic acid potassium salt | AmpC | 137.6647 |
| Clavulanic acid potassium salt | SHV-1 | 0.0303 |
| Clavulanic acid potassium salt | TEM-1 | 0.0295 |
| Sulbactam sodium salt | AmpC | 25.4954 |
| Sulbactam sodium salt | SHV-1 | 3.9150 |
| Sulbactam sodium salt | TEM-1 | 1.0659 |
| Tazobactam sodium salt | AmpC | 1.8082 |
| Tazobactam sodium salt | SHV-1 | 0.2220 |
| Tazobactam sodium salt | TEM-1 | 0.0172 |
| Example 1 | AmpC | 10.4476 |
| Example 1 | TEM-1 | 0.0666 |
| Example 2 | AmpC | 58.7670 |
| Example 2 | TEM-1 | 0.9454 |
| Example 3 | AmpC | 95.0730 |
| Example 3 | TEM-1 | 8.3863 |
| Example 4 | AmpC | 2.4695 |
| Example 4 | TEM-1 | 0.0890 |
| Example 5 | AmpC | 5.8200 |
| Example 5 | SHV-1 | 7.1435 |
| Example 5 | TEM-1 | 4.9233 |
| Example 6 | AmpC | 17.0795 |
| Example 6 | SHV-1 | 3.9503 |
| Example 6 | TEM-1 | 2.7923 |
| Example 7 | AmpC | 5.3763 |
| Example 7 | SHV-1 | 0.2169 |
| Example 7 | TEM-1 | 0.0784 |
| Example 8 | AmpC | 115.3075 |
| Example 8 | TEM-1 | 5.6422 |
| Example 9 | AmpC | 14.2710 |
| Example 9 | SHV-1 | 1.0430 |
| Example 9 | TEM-1 | 0.8275 |
| Example 10 | AmpC | 16.0350 |
| Example 10 | TEM-1 | 0.1399 |
| Example 11 | AmpC | 532.0000 |
| Example 11 | TEM-1 | 7.3067 |
| Example 12 | AmpC | 29.3960 |
| Example 12 | TEM-1 | 5.8977 |
| Example 13 | AmpC | 0.9943 |
| Example 13 | SHV-1 | 0.0477 |
| Example 13 | TEM-1 | 0.6394 |
| Example 14 | AmpC | 136.5686 |

| Compound | Enzyme | IC$_{50}$ [µM] |
|---|---|---|
| Example 14 | SHV-1 | 85.1150 |
| Example 14 | TEM-1 | 19.6320 |
| Example 15 | AmpC | 55.9574 |
| Example 15 | SHV-1 | 4.4272 |
| Example 15 | TEM-1 | 4.2683 |
| Example 16 | AmpC | 0.9414 |
| Example 16 | SHV-1 | 0.0805 |
| Example 16 | TEM-1 | 0.0652 |
| Example 17 | AmpC | 36.0330 |
| Example 17 | SHV-1 | 21.3035 |
| Example 17 | TEM-1 | 13.2596 |
| Example 18 | AmpC | 18.9543 |
| Example 18 | SHV-1 | 0.0139 |
| Example 18 | TEM-1 | 0.0271 |
| Example 19 | AmpC | 79.0345 |
| Example 19 | SHV-1 | 0.6166 |
| Example 19 | TEM-1 | 0.8706 |
| Example 24 | AmpC | 4.9780 |
| Example 24 | SHV-1 | 0.0622 |
| Example 24 | TEM-1 | 0.0306 |
| Example 26 | AmpC | 2.2006 |
| Example 26 | SHV-1 | 0.0363 |
| Example 26 | TEM-1 | 0.0092 |
| Example 27 | AmpC | 6.0248 |
| Example 27 | SHV-1 | 0.6243 |
| Example 27 | TEM-1 | 0.4261 |
| Example 28 | AmpC | 11.7498 |
| Example 28 | SHV-1 | 9.3179 |
| Example 28 | TEM-1 | 45.6844 |
| Example 32 | AmpC | 2.8648 |
| Example 32 | SHV-1 | 0.3390 |
| Example 32 | TEM-1 | 0.1215 |
| Example 34 | AmpC | 0.0884 |
| Example 34 | SHV-1 | 0.0503 |
| Example 34 | TEM-1 | 0.0217 |
| Example 35 | AmpC | 41.0621 |
| Example 35 | SHV-1 | 2.3072 |
| Example 35 | TEM-1 | 1.5615 |
| Example 36 | AmpC | 4.1861 |
| Example 36 | SHV-1 | 0.6423 |
| Example 36 | TEM-1 | 0.4076 |
| Example 37 | AmpC | 8.2748 |
| Example 37 | SHV-1 | 0.1413 |
| Example 37 | TEM-1 | 0.0442 |
| Example 38 | AmpC | 2.7249 |
| Example 38 | SHV-1 | 6.8103 |
| Example 38 | TEM-1 | 8.0160 |
| Example 38a | AmpC | 32.1830 |
| Example 38a | SHV-1 | 1.7131 |
| Example 38a | TEM-1 | 1.9486 |
| Example 39 | AmpC | 4.1188 |
| Example 39 | SHV-1 | 5.6099 |
| Example 39 | TEM-1 | 4.1249 |
| Example 40 | AmpC | 85.9540 |
| Example 40 | TEM-1 | 23.6215 |
| Example 41 | AmpC | 0.2854 |
| Example 41 | SHV-1 | 0.0004 |
| Example 41 | TEM-1 | 0.0002 |
| Example 42 | AmpC | 0.3848 |
| Example 42 | SHV-1 | 0.0008 |
| Example 42 | TEM-1 | 0.0017 |
| Mixture of Example 43 and Example 44 | AmpC | 0.1260 |
| Mixture of Example 43 and Example 44 | SHV-1 | 0.0043 |
| Mixture of Example 43 and Example 44 | TEM-1 | 0.0035 |
| Example 45 | AmpC | 1.0697 |
| Example 45 | SHV-1 | 0.0034 |
| Example 45 | TEM-1 | 0.0017 |
| Example 46 | AmpC | 0.3006 |
| Example 46 | SHV-1 | 0.0005 |
| Example 46 | TEM-1 | 0.0004 |
| Example 48 | AmpC | 0.3046 |
| Example 48 | SHV-1 | 0.0042 |
| Example 48 | TEM-1 | 0.0024 |
| Example 49 | AmpC | 6.0817 |
| Example 49 | SHV-1 | 0.0026 |
| Example 49 | TEM-1 | 0.0018 |
| Example 50 | AmpC | 26.9820 |
| Example 50 | SHV-1 | 0.0032 |
| Example 50 | TEM-1 | 0.0042 |
| Example 51 | AmpC | 414.6187 |
| Example 51 | SHV-1 | 0.4357 |
| Example 51 | TEM-1 | 0.2540 |
| Example 53 | AmpC | 0.5415 |
| Example 53 | SHV-1 | 0.2190 |
| Example 53 | TEM-1 | 0.0728 |
| Example 54 | AmpC | 3.4215 |
| Example 54 | SHV-1 | 0.2946 |
| Example 54 | TEM-1 | 0.0970 |
| Example 55 | TEM-1 | 118.4030 |
| Example 56 | AmpC | 57.4200 |
| Example 56 | TEM-1 | 17.7890 |
| Example 57 | AmpC | 5.3274 |
| Example 57 | SHV-1 | 0.0226 |
| Example 57 | TEM-1 | 0.0106 |
| Example 58 | AmpC | 4.5135 |
| Example 58 | SHV-1 | 0.0006 |
| Example 58 | TEM-1 | 0.0014 |
| Example 59 | AmpC | 6.4502 |
| Example 59 | SHV-1 | 3.6044 |
| Example 59 | TEM-1 | 4.3923 |

The antibacterial activity of the compounds of the present invention in combination with antibiotics is shown by the following examples:

In-Vitro Synergy Tests

Material and Methods

Antibacterial Agents:

Stock solutions of the test compounds and control antibiotics are prepared in distilled water according to the NCCLS guidelines (NCCLS (National Commitee for Clinical Laboratory Standards). 12(3). 2000. M7-A4). Lipophilic compounds with low water solubility are first dissolved in DMSO (dimethyl sulfoxide, 20%) and further diluted with water or Mueller Hinton Bouillon (MHB). All drug weights are corrected for salt forms and refer to the pure drug substance.

Bacterial Strains:

All tested strains and clinical isolates are either purchased from the American Type Culture Collection (ATCC), kindly supplied by A. Georgopoulos (Vienna General Hospital, Vienna, Austria), and I. Chopra (Leeds, UK), collected from the SENTRY study (F. J. Schmitz, Minden, Germany) or from the Sandoz culture collection.

All strain identities are confirmed by BBL Crystal™ Identification Systems (Beckton Dickinson, Cockeysville, Md., USA). Stock cultures are prepared from broth cultures grown at 35° C. for 18-22 h without agitation and subsequent addition of 5% DMSO (v/v, final concentration) as cryoprotectant and stored frozen in liquid nitrogen.

The presence of β-lactamase genes is proved by PCR using primers specific for the respective β-lactamase type.

Test Method

Bacterial susceptibility, expressed as MIC, is determined by microbroth dilution technique and agar dilution technique as recommended by the approved standard reference recommendations of the NCCLS. The selected antibiotics are diluted by serial twofold dilution ranging from either 256 µg/ml to 0.125 µg/ml or from 25.6 to 0.0125 µg/ml. When combined with β-lactamase inhibitor the inhibitor is added at a constant concentration of 17 or 68 µM.

The inoculum is prepared by the direct colony suspension method as described by NCCLS. For this purpose the bacteria are grown on blood agar plates at 35° C. for 24 h. Subsequently 3-5 single colonies are suspended in 5 ml liquid medium. The bacteria are then incubated for 5 h to reach the logarithmic growth phase and subsequently diluted with medium or NaCl (0.86%) to reach a final living cell count equivalent to $10^8$ CFU/ml. Then the bacterial suspension is diluted 1:10 and 1 μl ($10^4$ CFU; final inoculoum $10^5$ CFU/ml) is transferred to the test medium containing the antibacterial substances by a multipoint inoculator (Dynatech, Chantilly, Va., USA). The plates are then incubated at 35° C. for 24 h. The MIC is determined optically and defined as the minimum inhibitory concentration [μg/ml] of antibiotic at which no visible bacterial growth occurs.

Minimum Inhibitor Concentrations (MIC) of Amoxicillin, Ceftazidime and Cefepime Alone and in the Presence of Compound of Example 49 in the Specified Concentration

|  | ATCC Nr. | Amoxicillin MIC, μg/ml | | Ceftazidime MIC, μg/ml | | Cefepime MIC, μg/ml | |
| --- | --- | --- | --- | --- | --- | --- | --- |
|  |  | alone | +68 μM Example 49 | alone | +68 μM Example 49 | alone | +17 μM Example 49 |
| K. pneumoniae | 700603 | >25.6 | 3.2 | >25.6 | 0.2 | 0.8 | 0.2 |
| E. cloacae | 83989 | Not tested | Not tested | >25.6 | 12.8 | 0.8 | 0.8 |
| C. freundii | 7023771 | Not tested | Not tested | >25.6 | 3.2 | 0.8 | 0.4 |

Pharmakokinetics

Compounds of the present invention show bioavailability in animals after subcutane or p.o. administration, as shown in the following examples.

The compound of Example 49 resulted after oral application of 25 mg/kg (formulated in 650 mg cremophor EL+1 ml 96% ethanol+4.575 ml 5% glucose in saline) to mice in a peak plasma concentration ($C_{max}$) of 2.22 μg/ml after 15 minutes, the $AUC_{tot}$ reached 65.123 μg/ml*minutes, and the $T_{half}$ was 18.90 minutes.

The subcutaneous application of 10 mg/kg (in 0.05 M $NaPO_4$ buffer, pH 7.2) to mice resulted in a $C_{max}$ of 5.6 μg/ml after 5 minutes, the $AUC_{tot}$ was 125.65 μg/ml*min, and a $T_{half}$ of 12.27 minutes was reached.

The values of the PK parameters were calculated by standard noncompartmental analysis, using Kinetica 4.2 (InnaPhase). Plasma concentration values below the limit of quantification were taken as 0. The maximum plasma concentration ($C_{max}$) and the time to reach $C_{max}$ were determined from observed data.

In-Vivo Antibacterial Activity

Compounds of the present invention upon coadministration of an antibiotic show antibacterial activity in animals as shown in the following examples.

A sepsis model in female NMRI mice was employed using TEM-1 producing E. coli B269 (clinical isolate) as the infecting bacterial strain. In general, the final inoculum given in 0.3 ml per mouse intraperitoneally represented a 100% lethal concentration for systemic infections within 48 hours.

A combination of the β-lactam antibiotic cefepime with the compound of Example 49 was compared to cefepime alone. The subcutaneous treatment schedule for the antibiotic at various doses was simultaneous and 3 hours after infection. The test compound (compound of Example 49) was given by the same route at a fixed dose of 20 mg/kg simultaneously, 1.5, 3, and 4.5 hours after infection.

After treatment with the combination of cefepime and the test compound, a dose of e.g. 0.5 mg/kg cefepime lead to survival of all animals in this treatment group, whereas after treatment with comparable doses of the antibiotic alone no animals survived.

The invention claimed is:

1. A compound of formula I

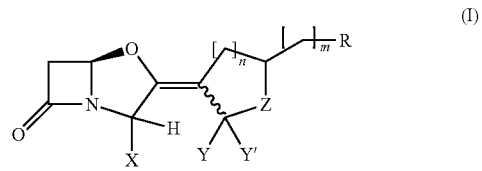

wherein
X is:
COOH or salts thereof,
$COOR_1$, wherein $R_1$ is $C_{1-4}$ alkyl which is optionally substituted,
$CONR_2R_3$, wherein $R_2$ and $R_3$ independently represent H or $C_{1-5}$ alkyl, or $C_{5-6}$ cycloalkyl, which optionally contains one or more hetero atoms selected from O, S and N and/or is optionally substituted, or
$CON(R_2)$—$CH(R_4)$—$R_5$, wherein
$R_2$ is as defined above,
$R_4$ is methyl or benzyl, and
$R_5$ is COOH or a salt thereof; $COOR_1$, wherein $R_1$ is as defined above; or
$CONR_2R_3$, wherein $R_2$ and $R_3$ are as defined above,
Y and Y' are both H or together represent =O,
Z is O, $NR_2$ or N—$CH(R_4)$—$R_5$, wherein $R_2$, $R_4$ and $R_5$ are as defined above,
n is 1 or 2,
m is a number from 0 to 4, and
R is H, or
a saturated or unsaturated chain containing 1 to 8 carbon atoms, which is optionally substituted by a 5 or 6-membered nonaromatic ring containing one or more hetero atoms selected from O, S and N, or by aryl, alkyl or cycloalkyl, optionally containing one or more hetero atoms selected from O, S and N, and/or is optionally substituted with one or more heteroatoms selected from O, S and N, halogens Cl, Br, I and F and/or azido $N_3$.

2. The compound according to claim 1, in a pharmaceutically acceptable salt form.

3. The compound according to claim 1, wherein $R_1$ is methyl.

4. The compound according to claim 1, wherein $R_2$ and $R_3$ are independently substituted $C_{1-4}$ alkyl or $C_{5-6}$ cycloalkyl.

5. The compound according to claim 1, wherein $R_4$ is methyl.

6. The compound according to claim 1, wherein R is a saturated or unsaturated chain containing 1 to 8 carbon atoms which is optionally substituted by an 5 or 6-membered nonaromatic ring, containing one or more hetero atoms selected from O, S and N, or by aryl, alkyl or cycloalkyl.

7. The compound according to claim 1, wherein R is a saturated or unsaturated chain containing 1 to 8 carbon atoms which is substituted by one or more heteroatoms selected from O, S, and N, wherein the O and S heteroatoms are protected as esters, carbonates or ethers, and the N heteroatoms are alkylated or protected as amides or carbamates.

8. The compound according to claim 1, having formula III

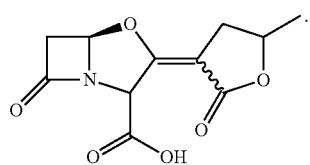
(III)

9. A pharmaceutical composition comprising a compound according to claim 1, optionally further comprising a β-lactam antibiotic belonging to the class of penicillins or cephalosporins.

10. The compound according to claim 1, wherein $R_4$ is benzyl.

11. A compound of formula I

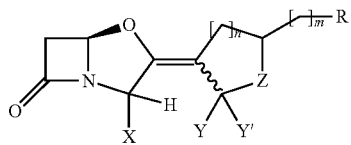
(I)

wherein
X is
  COOH or salts thereof,
  $COOR_1$, wherein $R_1$ is $C_{1-4}$ alkyl which is optionally substituted,
  $CONR_2R_3$, wherein $R_2$ and $R_3$,
    independently represent H, or $C_{1-5}$ alkyl, or $C_{5-6}$ cycloalkyl, which optionally contains one or more hetero atoms selected from O, S and N and/or is optionally substituted, or $CON(R_2)$—$CH(R_4)$—$R_5$, wherein
    $R_2$ is as defined above,
    $R_4$ is methyl or benzyl, and
    $R_5$ is COOH or a salt thereof; $COOR_1$, wherein $R_1$ is as defined above; or
    $CONR_2R_3$, wherein $R_2$ and $R_3$ are as defined above,
Y and Y' together represent =O,
Z is O, $NR_2$ or N—$CH(R_4)$—$R_5$, wherein $R_2$, $R_4$ and $R_5$ are as defined above,
n is 1 or 2,
m is a number from 0 to 4, and
R is H, or
  a saturated or unsaturated chain containing 1 to 8 carbon atoms, which is optionally substituted by a 5 or 6-membered nonaromatic ring containing one or more hetero atoms selected from O, S and N, or by aryl, alkyl or cycloalkyl, optionally containing one or more hetero atoms selected from O, S and N, and/or is optionally substituted with one or more heteroatoms selected from O, S and N, halogens Cl, Br, I and F and/or azido $N_3$.

12. A compound of formula I

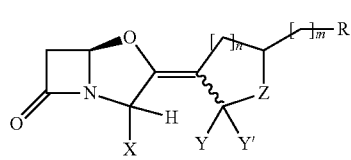
(I)

wherein
X is
  COOH or salts thereof,
  $COOR_1$, wherein $R_1$ is methyl,
  $CONR_2R_3$, wherein $R_2$ and $R_3$ are independently substituted $C_{1-4}$ alkyl or $C_{5-6}$ cycloalkyl, or
  $CON(R_2)$—$CH(R_4)$—$R_5$, wherein
    $R_2$ is as defined above,
    $R_4$ is methyl or benzyl and
    $R_5$ is COOH or a salt thereof; $COOR_1$, wherein $R_1$ is as defined above; or
    $CONR_2R_3$, wherein $R_2$ and $R_3$ are as defined above,
Y and Y' together represent =O,
Z is O, $NR_2$ or N—$CH(R_4)$—$R_5$, wherein $R_2$, $R_4$ and $R_5$ are as defined above,
n is 1 or 2,
m is a number from 0 to 4, and
R is H, or
  a saturated or unsaturated chain containing 1 to 8 carbon atoms, which is optionally substituted by a 5 or 6-membered nonaromatic ring containing one or more hetero atoms selected from O, S and N, or by aryl, alkyl or cycloalkyl, optionally containing one or more hetero atoms selected from O, S and N, and/or is optionally substituted with one or more heteroatoms selected from O, S and N, halogens Cl, Br, I and F and/or azido $N_3$.

13. A compound according to claim 1 of formula I

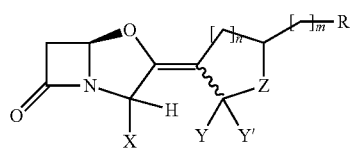
(I)

wherein
X is
  $CON(R_2)$—$CH(R_4)$—$R_5$, wherein
    $R_2$ is substituted $C_{1-4}$ alkyl or $C_{5-6}$ cycloalkyl,
    $R_4$ is methyl or benzyl, and
    $R_5$ is
      COOH or a salt thereof; $COOR_1$, wherein $R_1$ is methyl; or $CONR_2R_3$, wherein $R_2$ and $R_3$ independently are substituted $C_{1-4}$ alkyl or $C_{5-6}$ cycloalkyl,
Y and Y' are both H or together represent =O,
Z is O, $NR_2$ or N—$CH(R_4)$—$R_5$, wherein $R_2$, $R_4$ and $R_5$ are as defined above,
n is 1 or 2,
m is a number from 0 to 4, and
R is H, or
  a saturated or unsaturated chain containing 1 to 8 carbon atoms, which is optionally substituted by a 5 or 6-membered nonaromatic ring containing one or more hetero atoms selected from O, S and N, or by aryl, alkyl or cycloalkyl, optionally containing one or more hetero atoms selected from O, S and N, and/or is optionally substituted with one or more heteroatoms selected from O, S and N, halogens Cl, Br, I and F and/or azido $N_3$.

14. The compound according to claim 13, wherein $R_4$ is benzyl.

15. The compound according to claim 13, wherein $R_4$ is methyl.

16. The compound according to claim 5 in a pharmaceutically acceptable salt form.

17. The compound according to claim 11 in a pharmaceutically acceptable salt form.

18. The compound according to claim 12 in a pharmaceutically acceptable salt form.

19. The compound according to claim 13 in a pharmaceutically acceptable salt form.

20. The compound according to claim 10 in a pharmaceutically acceptable salt form.

* * * * *